US009956395B2

(12) United States Patent
Bikson et al.

(10) Patent No.: US 9,956,395 B2
(45) Date of Patent: May 1, 2018

(54) ELECTRODE ASSEMBLY

(75) Inventors: Marom Bikson, Brooklyn, NY (US);
Gregory Kronberg, Syosset, NY (US);
Tamer N. Naguib, Staten Island, NY (US); Denis Arce, Flushing, NY (US);
Preet Minhas, Richmond Hill, NY (US)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 1045 days.

(21) Appl. No.: 13/880,258

(22) PCT Filed: Oct. 19, 2011

(86) PCT No.: PCT/US2011/056863
§ 371 (c)(1),
(2), (4) Date: Jun. 24, 2013

(87) PCT Pub. No.: WO2012/054587
PCT Pub. Date: Apr. 26, 2012

(65) Prior Publication Data
US 2013/0268038 A1    Oct. 10, 2013

Related U.S. Application Data

(60) Provisional application No. 61/394,636, filed on Oct. 19, 2010, provisional application No. 61/488,364, filed on May 20, 2011.

(51) Int. Cl.
*A61N 1/04* (2006.01)
*A61N 1/05* (2006.01)
*A61N 1/36* (2006.01)

(52) U.S. Cl.
CPC ......... *A61N 1/0526* (2013.01); *A61N 1/0472* (2013.01); *A61N 1/36025* (2013.01); *A61N 1/0456* (2013.01)

(58) Field of Classification Search
CPC .............. A61N 1/36025; A61N 1/0456; A61N 1/36014; A61N 1/006; A61N 1/36021;
(Continued)

(56) References Cited

U.S. PATENT DOCUMENTS 3,998,215 A    12/1976  Anderson et al.
4,603,704 A    8/1986   Mund et al.
(Continued)

FOREIGN PATENT DOCUMENTS

FR       2452938       10/1980
WO       WO9965389     12/1999
(Continued)

*Primary Examiner* — Amanda Patton
(74) *Attorney, Agent, or Firm* — Hoffmann & Baron, LLP

(57) ABSTRACT

An electrode assembly includes a substantially porous element configured to be coupled to an electrode for delivery of electrical current to a patient in a neurostimulation procedure. The substantially porous material defining a contact surface, of which at least a portion contacts the patient during the neurostimulation procedure. A first insulating member is coupled to the substantially porous element and exposed at the contact surface to prevent a portion of the contact surface from contacting the patient to deliver the electrical current during the neurostimulation procedure.

24 Claims, 33 Drawing Sheets

(58) Field of Classification Search
CPC ...... A61N 1/0408; A61N 1/0484; A61N 1/40;
A61N 1/0476; A61N 1/0492; A61N
1/0472; A61N 1/20; A61N 1/205; A61N
1/303; A61N 1/18; A61N 2007/0026
USPC ........................................................ 607/116
See application file for complete search history.

(56) References Cited

U.S. PATENT DOCUMENTS

| | | | |
|---|---|---|---|
| 4,919,148 A | | 4/1990 | Muccio |
| 5,038,796 A | * | 8/1991 | Axelgaard ............ A61N 1/0452 607/152 |
| 5,199,438 A | * | 4/1993 | Pearlman ............ A61B 5/02028 600/483 |
| 6,038,464 A | * | 3/2000 | Axelgaard ......... A61B 5/04087 600/391 |
| 6,324,429 B1 | | 11/2001 | Shire et al. |
| 2003/0069627 A1 | | 4/2003 | Giuntoli et al. |
| 2003/0078646 A1 | * | 4/2003 | Axelgaard ............ A61N 1/0472 607/142 |
| 2003/0176908 A1 | | 9/2003 | Lin |
| 2011/0137381 A1 | * | 6/2011 | Lee ...................... A61N 1/0529 607/62 |

FOREIGN PATENT DOCUMENTS

| | | |
|---|---|---|
| WO | WO2009137683 | 11/2009 |
| WO | WO2010078441 | 7/2010 |

\* cited by examiner

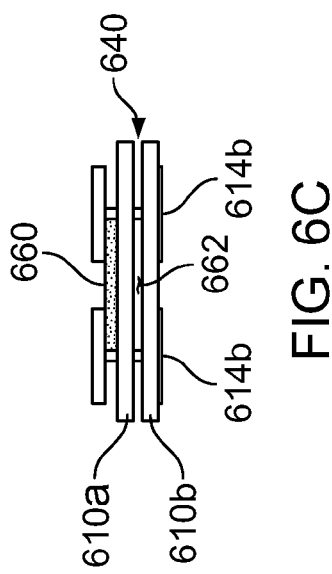
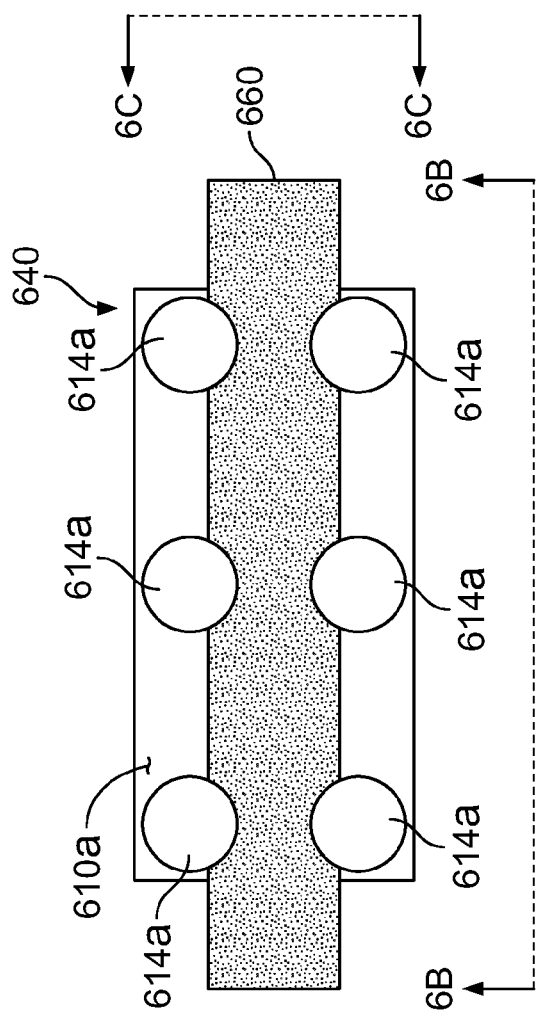
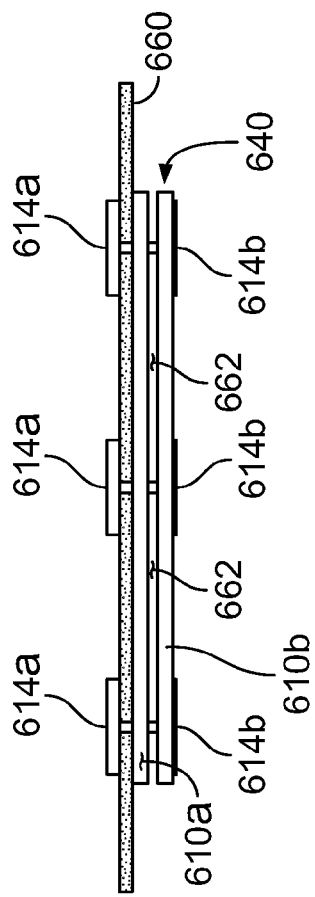

ELECTRODE ASSEMBLY

CROSS REFERENCE TO RELATED APPLICATIONS

This application claims the benefit under 35 U.S.C. § 119(e) of U.S. Patent Application No. 61/394,636, entitled "Transcranial electrical stimulation and system and methods thereof," filed Oct. 19, 2010. This application also claims the benefit of U.S. Patent Application No. 61/488,364, entitled "Method and apparatus for positioning of electrodes on the head," filed May 20, 2011.

The disclosure of each prior application is incorporated herein by reference in its entirety.

FIELD OF THE INVENTION

This disclosure relates to an electrode assembly and also systems and methods for delivering neurostimulation, such as transcranial direct current stimulation ("tDCS") to a patient, using the electrode assembly.

BACKGROUND

Neurostimulation involves modulating the nervous system and electrically activating neurons in the body. Transcranial direct current stimulation (tDCS) is a form of neurostimulation that uses constant, low current delivered directly to particular areas of the brain using electrodes. tDCS can be used, for example, as therapy for certain psychological disorders, such as anxiety disorders and depression.

SUMMARY OF THE INVENTION

In one aspect, an electrode assembly includes a substantially porous element configured to be coupled to an electrode for delivery of electrical current to a patient in a neurostimulation procedure. The substantially porous material defines a contact surface, at least a portion of which contacts the patient during the neurostimulation procedure. A first insulating member (e.g., a rivet) is coupled to the substantially porous element and exposed at the contact surface to prevent a portion of the contact surface from contacting the patient to deliver the electrical current during the neurostimulation procedure.

In some implementations, the substantially porous element has one or more edges that extend from the contact surface. In those implementations, the first insulating member is exposed at the contact surface near one of the edges. In certain embodiments, the first insulating member is positioned so that an outermost point of the exposed portion is no further from the nearest edge than approximately 50% of the exposed portion's width.

The substantially porous element, in some embodiments, has a corner at a point where the contact surface and two of the edges connect to one another and the first insulating member is exposed at the contact surface near the corner.

According to certain implementations, the substantially porous element has one or more edges at which an opening is provided for receiving and gripping the electrode in a manner that facilitates a low resistance electrical connection between the substantially porous element and the electrode.

A portion of the substantially porous material can be exposed at the contact surface between the exposed portion of the first insulating member and edge of the first insulating member that is closest to the exposed portion.

In certain embodiments, the substantially porous element includes a first portion and a second portion. The first insulating member is configured to physically hold together the first portion and the second portion. In some instances, the first insulating member includes a substantially cylindrical portion (that may or may not include two portions joined together) that extends through the first and second portions of the substantially porous member and a head at each end of the substantially cylindrical portion, wherein each head has a larger diameter than the substantially cylindrical portion.

The first insulating member can be, for example, a rivet, a pin pushed into the contact surface of the substantially porous element or a sticker or adhesive material adhered to the contact surface of the substantially porous element.

In some implementations, the substantially porous material is configured to absorb and at least partially contain an electrolyte in liquid form.

In a typical embodiment, a second insulating member is coupled to the substantially porous element and exposed at the contact surface. The first and second insulating members are spaced sufficiently far apart from one another so that the electrode can fit between the first and second insulating members.

In another aspect, an electrode assembly includes a substantially porous element having a contact surface, at least a portion of which is configured to contact a patient during delivery of electrical current from the substantially porous element to the patient during a neurostimulation procedure, wherein the substantially porous element includes a first portion and a second portion. Two or more rivets are provided that are made of electrically insulating material and that pass through the first portion and second portion of the substantially porous element to hold the first and second portion together. Each rivet has a head portion exposed at the contact surface to prevent a portion of the contact surface from contacting the patient during the neurostimulation procedure. The rivets are positioned so that an innermost portion of each respective head is no further from a closest edge of the substantially porous element than approximately 150% of the head's diameter.

In yet another aspect, a system includes a neurostimulation device (e.g., a tDCS device), at least two electrically conductive cables coupled to the neurostimulation device; an electrode coupled to the distal end of each respective one of the electrically conductive cables; and an electrode interface optionally removably coupled to at least one of the electrodes. Each electrode interface includes a substantially porous element physically coupled to the electrode for delivery of electrical current to a patient in a neurostimulation procedure. The substantially porous material defines a contact surface. At least a portion of the contact surface contacts the patient during the neurostimulation procedure. A first insulating member is coupled to the substantially porous element and exposed at the contact surface to prevent a portion of the contact surface from contacting the patient to deliver the electrical current during the neurostimulation procedure.

In some implementations, the substantially porous element has one or more edges that extend from the contact surface, and the first insulating member is positioned so that an outermost point of the exposed portion is no further from the nearest edge than approximately 50% of the exposed portion's width.

The substantially porous element typically has a corner at a point where the contact surface and two of the edges connect to one another and the first insulating member is exposed at the contact surface near the corner. According to certain embodiments, the substantially porous element has one or more edges at which an opening is provided for receiving and gripping the electrode in a manner that facilitates a low resistance electrical connection between the substantially porous element and the electrode.

A portion of the substantially porous material typically is exposed at the contact surface between the exposed portion of the first insulating member and edge of the first insulating member that is closest to the exposed portion.

In some implementations, the substantially porous element has a first portion and a second portion. The first insulating member is configured to physically hold together the first portion and the second portion and the electrode is positioned between the first portion and the second portion of the substantially porous element.

The first insulating member can be a rivet with a substantially cylindrical portion that extends through the first and second portions of the substantially porous member and a head at each end of the substantially cylindrical portion. Each head typically has a larger diameter than the substantially cylindrical portion.

In certain embodiments, a second insulating member is coupled to the substantially porous element and exposed at the contact surface. The first and second insulating members are spaced sufficiently far apart from one another so as to accommodate the electrode, which is positioned between the first and second insulating members.

According to some implementations, a second insulating member is coupled to the substantially porous element and exposed at the contact surface. The first and second insulating members are exposed at a surface of the substantially porous material opposite the contact surface. In those instances, the system further includes a strap for coupling the electrode interface to the patient. The strap can be, for example, between portions of the first and second insulating members that are exposed at the surface of the substantially porous material opposite the contact surface and the portions of the first and second insulating members extend over the strap to thereby couple the electrode interface to the strap.

The first insulating member can be, for example, a pin pushed into the contact surface of the substantially porous element or a sticker or adhesive material adhered to the contact surface of the substantially porous element.

The substantially porous material is adapted to and typically does contain an electrolyte in liquid form during the delivery of electrical current.

In some implementations, for electrodes greater than 5 cm2, for electrolytes with resistivity more than triple of saline solution, or when a porous material (sponge) density is used, or small pore size, or large inter-pore distance is present, such that the resulting resistivity of the sponge is more than triple that of saline solution, then it may be desirable to increase the porous material thickness between the electrode and the skin to about 0.75 cm (i.e., three times 0.25 cm).

In a typical implementation, the conductive rubber insert (of the electrode), when used in a sponge pocket, is greater than about 1 cm2 and preferably greater than about 4 cm2. An increase area of the rubber inset facilitates greater dispersion of current prior to reaching the skin. For sponge thickness of less than about 0.5 cm, the size of the rubber inset or other electrode can be increased in area such that, in some instances, the distance from the edge of the rubber inset to the edge of the sponge pocket is less than about 1 cm. This can, in certain implementations, facilitate current reaching sponge edges including when higher resistivity porous material is used.

According to certain embodiments, the conductive rubber inset is not insulated on either surface such that current may exit from the rubber inset into both the top and bottom porous material which may, in some instances, enhance the spread of current toward the electrode edges. For this reason, the presence of a porous material with electrolyte over the rubber inset allows for current to exit from the top surface of the sponge. In some instances, it may be desirable for the thickness of the porous material over the rubber inset to be greater than about 0.25 cm and preferably greater than about 0.5 cm. The thickness of the top porous material can be less than then bottom porous material. Using a thinner top porous material, in some instances, reduces the overall thickness of the sponge.

The conductive rubber inset may be replaced with a metal material where the metal material has a largely planar structure preferably allowing it to be placed on the surface of one of the porous materials. If the exposed area of the metal is less than about 2 cm2, and especially if is less than about 1 cm2, then, in some instances, more than one conductor may be inserted into the sponges thus effectively increasing the total area of metal contacting the sponge to the combined area of the metal electrodes. For example, 4 electrodes of approximately 1 cm2 can be positioned in one sponge and arranged such a line drawn between the centers of the electrode approximates a 4 cm×4 cm square. Preferably, sintered silver-chloride is used for the metal electrode, or gold, of platinum.

The average size of pores on the porous material can range from about 80 microns to about 200 microns giving flexibility in the electrolyte uptake by the material. On average, the volumetric expansion of the sponges can be about 0.15 cm$^3$; that is about 0.5 cm on the base (length), about 0.5 cm on the width, and about 6% (0.6 cm) on the thickness.

As an example, the porous material can be made, for example, from polyvinyl alcohol (PVA) and Glycerin. The porous material may contain reinforcing fibers (threads) that enhance certain mechanical properties of the material and its durability.

In some implementations, one or more of the following advantages are present. For example, a structurally sound, low pain electrode assembly can be produced.

Other features and advantages will be apparent from the description and drawings, and from the claims.

BRIEF DESCRIPTION OF THE DRAWINGS

FIG. 6A to 6C are views of an electrode assembly coupled to a strap for coupling to a patient.

Like reference characters in the drawings refer to like elements.

DETAILED DESCRIPTION

The present application relates to an electrode assembly and systems and methods for delivering neurostimulation, such as transcranial direct current stimulation ("tDCS") to a patient, using the electrode assembly.

In general, tDCS uses a relatively constant, low flow of direct electrical current delivered directly to the brain area of a patient using small electrodes placed on the patient's skin (i.e., not directly on the patient's brain). More particularly, when the electrodes are placed in or near the regions of interest, electrical current flow through the electrodes induces intracerebral current flow. This intracerebral current flow can either increase or decrease neuronal excitability in specific areas being stimulated based on which type of stimulation is being used. This change of neuronal excitability leads to alteration of brain function, which can be used in various therapies as well as to provide more information about the functioning of the human brain. For example, tDCS can be used as therapy for certain physicological disorders, such as anxiety disorders and depression, as well as a tool for motor rehabilitation in stroke patients.

The neurostimulation and tDCS techniques disclosed herein are completely noninvasive and, therefore, easy to administer, safe and convenient for patients or recipients of the tDCS.

Figure 1:
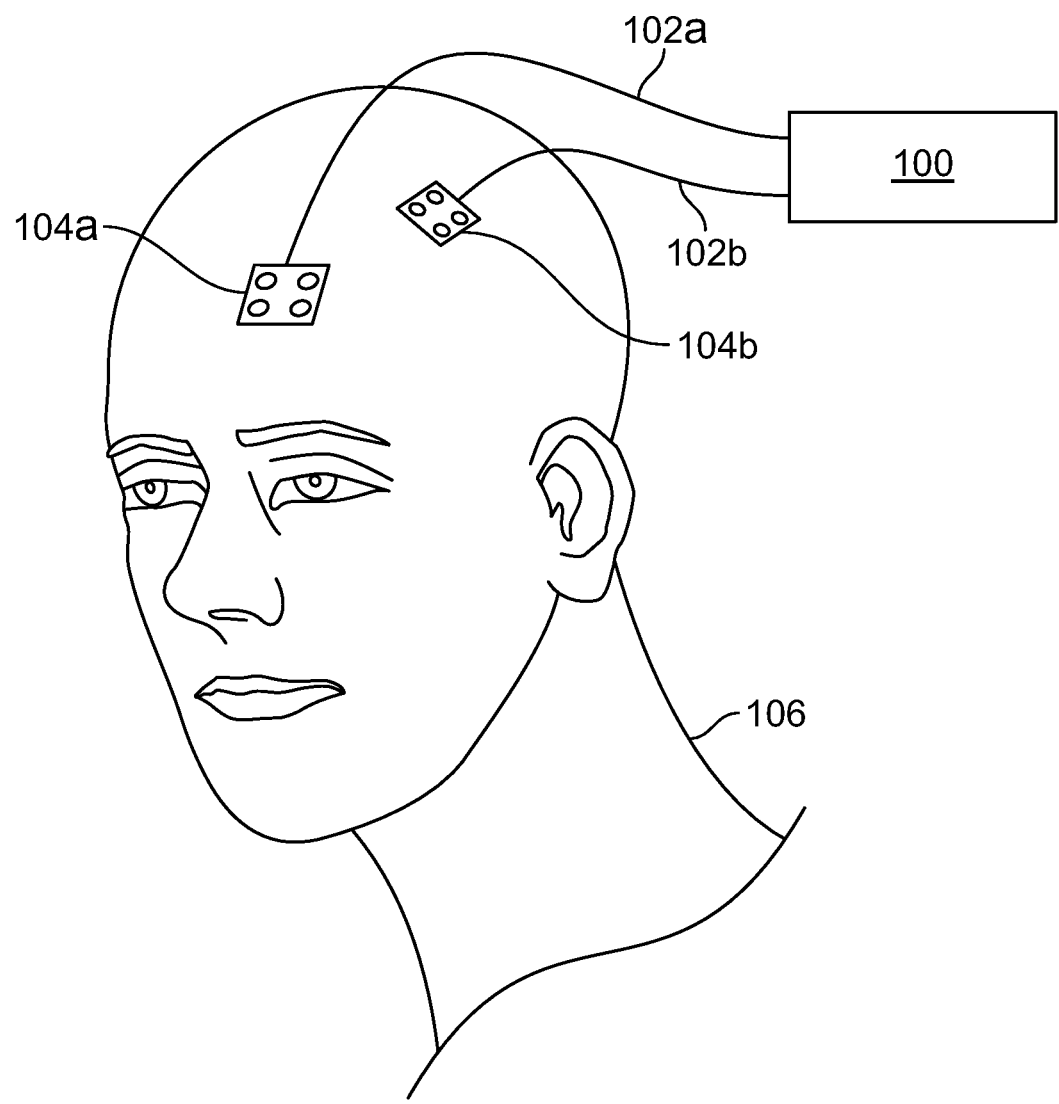
FIG. 1 is a perspective view of a transcranial direct current stimulation ("tDCS") system coupled to a patient.

FIG. 1 shows an exemplary tDCS device 100 connected via a pair of electrical cables 102a, 102b to electrode assemblies 104a, 104b at their respective distal ends, which are in contact with the head of a human patient 106. There are a variety of ways that the electrode assemblies 104a, 104b can be secured to the patient's head including, for example, with an adhesive substance, with a strap or tape, by virtue of the electrode assemblies being integrated into a cap that the patient wears on his or her head. In the illustrated example, a first one of the electrode assemblies 104a is positioned near a front portion of the patient's head and a second one of the electrode assemblies 104b is positioned back on the top of the patient's head, displaced at least several centimeters away from the first electrode 104a. Of course, a variety of electrode configurations are possible.

In a typical implementation, before the actual tDCS is initiated, a human operator would program into the tDCS device 100 at least: 1) a target value of current; and 2) a duration for delivering the target value of current to the human patient 106. Prior to delivery of current, the human operator positions the electrodes, prepares them (e.g., by adding fluid, such as an electrolyte) and/or checking the resistance of the electrode connections to the patient If all is in order, then, the human operator prompts the tDCS device 100 to begin producing electrical current. In response to this prompt (or in response to some other external trigger), the tDCS device 100 begins producing electrical current. More particularly, in response to the prompt from the human operator, the tDCS device 100 ramps the flow of electrical current from zero up to the target current value, delivers the target current value for approximately the duration that was specified by the human operator, and then ramps the flow of electrical current back to zero. In one implementation, while electrical current is being produced, it flows from the tDCS device 100 to the human patient 106 via the electrical cable 102a and the first electrode assembly 104a (the anodal electrode assembly) and returns to the tDCS device 100 via the second electrode assembly 104b (the cathodal electrode assembly) and the second electrical cable 102b.

In general, electrical current flow produces heat. In some implementations, when electrical current is being delivered to a patient during transcranial direct current stimulation, or the like, heat produced at the interface of the electrode assemblies 104a, 104b and the patient's skin can cause the patient 106 to experience an often high degree of discomfort while the electrical current is flowing. In the illustrated implementation, the electrode assemblies 104a, 104b are configured, as discussed herein, in such a manner as to minimize the likelihood that the patient receiving the flow of electrical current will experience a high degree of discomfort.

Figure 2:
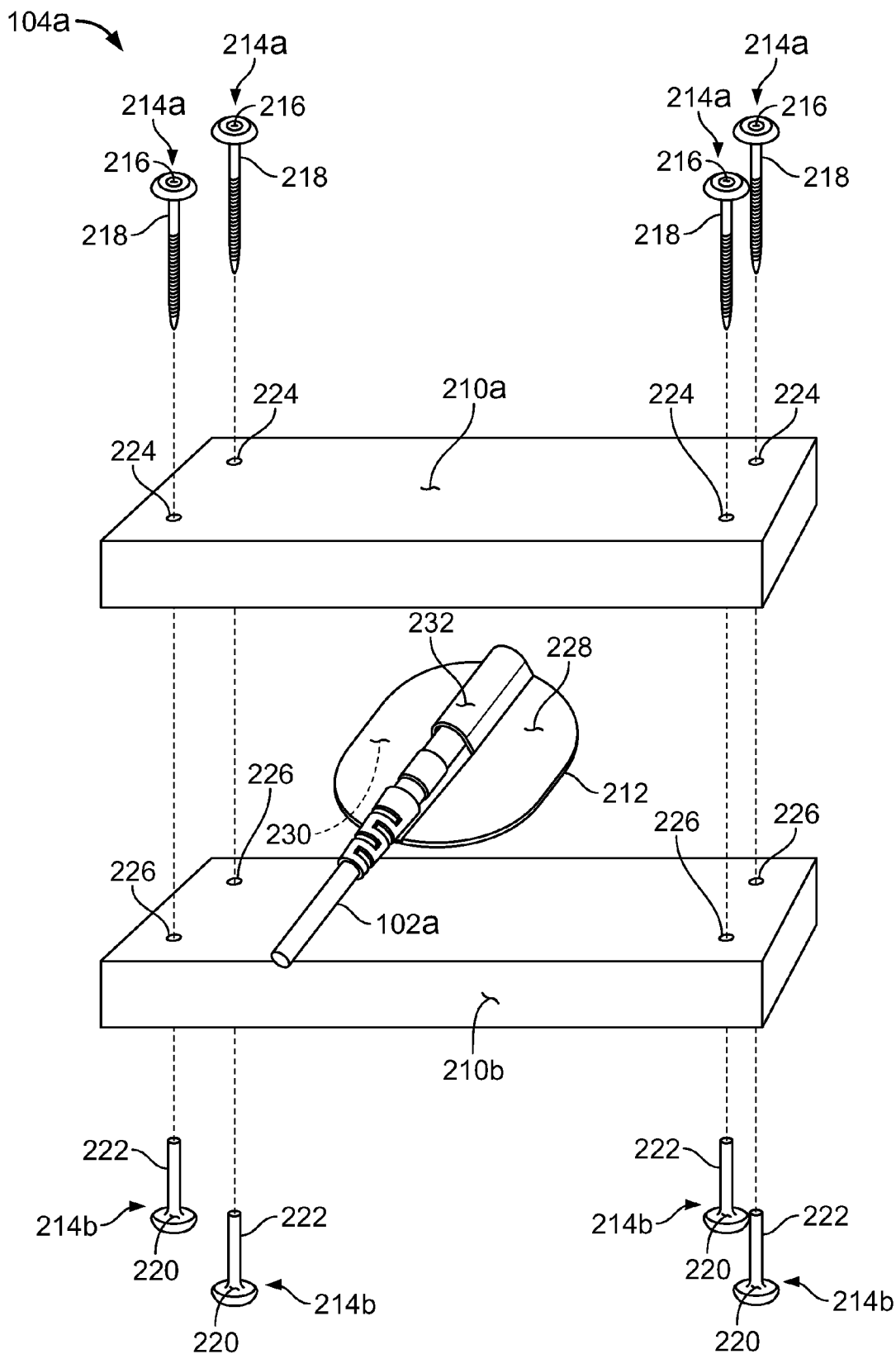
FIG. 2 is an exploded view of an electrode assembly in the tDCS system of FIG. 1.

FIG. 2 shows an exploded view of the first (anodal) electrode assembly 104a from FIG. 1

The illustrated assembly 104a includes an upper substantially porous element, in the form of upper sponge 210a, a lower substantially porous element in the form of lower sponge 210b, an electrode 212 between the upper and lower sponges 210a, 210b and an electrical cable coupled to the electrode 212. The illustrated assembly 104a also includes a plurality of insulating members, in the form of rivets 214a/214b that are coupled to the upper and lower sponges 210a, 210b. Each rivet 214a/214b has an upper portion 214a with a head 216 and a shaft 218 and a lower portion 214b with a head 220 and a shaft 222.

In a typical implementation, the upper and lower sponges 210a, 210b are electrode sponges, particularly adapted for use in connection with neurostimualtion procedures, such as tDCS. Typically, the upper and lower sponges 210a, 210b are adapted to receive and contain an electrolytic solution to facilitate conduction during the procedure. The rivets, in contrast, are typically rigid elements that are not electrically conductive or at least have substantially lower conductivity than the sponges saturated with electrolyte.

The rivets are typically electrically insulating. Some suitable materials for the rivets include glass, Teflon, rubber, plastics, a conductive material that is at least partially covered with an insulating layer, etc.

When the electrode assembly 104a is assembled, the aligned shafts 218, 222 pass through the upper and lower sponges 210a, 210b to engage one another and hold the upper and lower sponges 210a, 210b together. In a typical implementation, the upper and lower sponges 210a, 210b are held together in such a manner that a human operator can easily slide an electrode (e.g., electrode 212) in between the upper and lower sponges 210a, 210b. Additionally, in a typical implementation, the upper and lower sponges 210a, 210b are held together in such a manner that they can grip an electrode (e.g., electrode 212) positioned in between the upper and lower sponges 210a, 210b.

When the electrode assembly 104a is assembled, the upper rivet heads 216 are exposed at an outer surface (facing upward in FIG. 2) of the upper sponge 210a and the lower rivet heads 220 are exposed at an outer surface (not visible, but facing downward in FIG. 2) of the lower sponge 210b. In a typical implementation, to deliver tDCS to a patient, at least a portion of the outer surface (not visible, but facing downward in FIG. 2) of the lower sponge 210b (including the lower rivet heads 220) would be positioned in physical contact with the skin (or skin and hair) of the human patient. Indeed, in most implementations, the entire outer surface of the lower sponge 210b, including the lower rivet heads, come into contact with the patient's skin during tDCS.

As discussed in further detail herein, in a typical implementation, the rivets and, particularly, the lower rivet heads exposed at the outer surface of the lower substantially porous material, help reduce the likelihood that a person receiving tDCS (or other types of neurostimulation) will experience discomfort. It is believed that this is generally due to a redistribution of electrical current flowing out of the bottom surface of the lower sponge that results from the exposed head of the non-conductive rivets at that surface.

In a typical implementation, the rivet heads 216, 220 are flat or at least substantially flat and, therefore, lie substantially in (or extend only slight out of) the planes associated with the outer surfaces of the upper and lower sponges 210a, 210b.

In the illustrated embodiment, the electrode 212 includes a flat, substantially disk-shaped portion 228 that may be, for example, an electrically conductive silicon rubber material, or the like. The disk-shaped portion has a substantially flat bottom surface 230 that comes into intimate contact with at least a portion of the lower sponge 210b when assembled. The disk-shaped portion has a plug connection 232 at its upper surface that provides an electrical socket adapted to receive and engage the electrical cable 102a that delivers electrical current from the tDCS device 100 both physically and electrically.

During operation, electrical current flows into the electrode 212 from the electrical cable 102a and flows from the disk-shaped portion 228 into the lower sponge 210b to the patient.

Figure 3A:
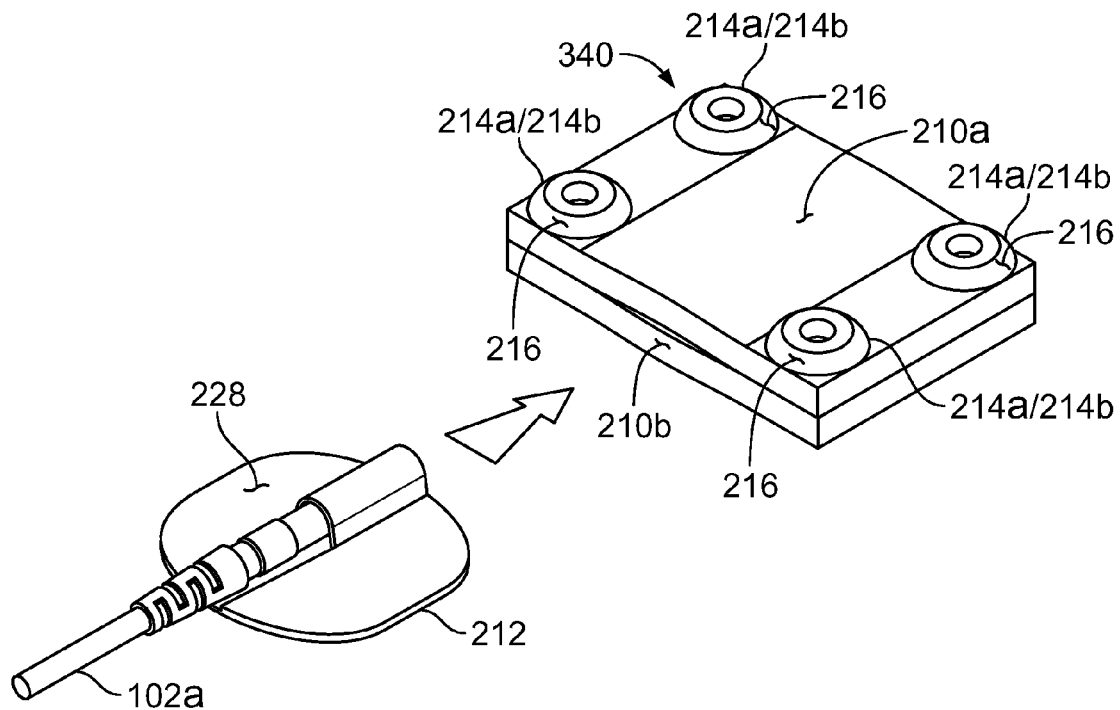
FIGS. 3A and 3B are perspective views of an electrode being pushed between sponges in an electrode interface device.
Figure 3B:
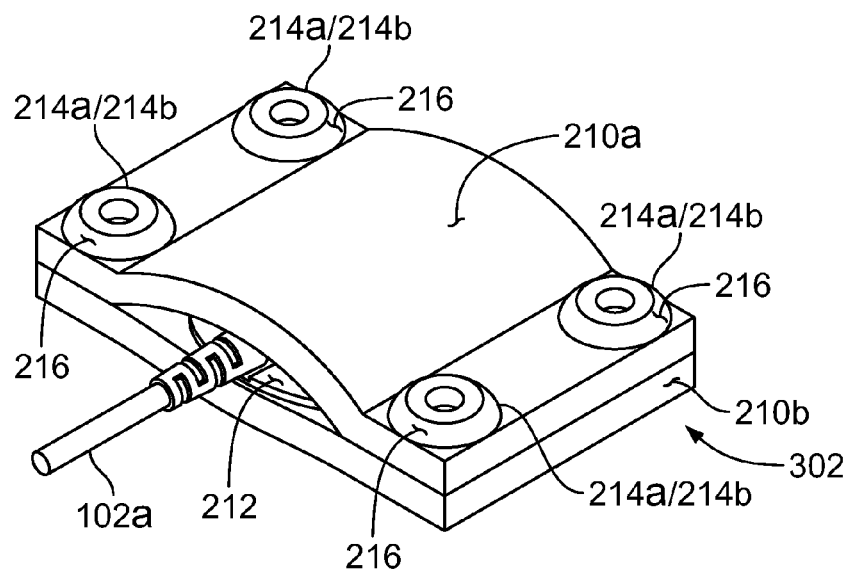

FIGS. 3A and 3B are perspective views showing the electrode 212 of FIG. 2 being slid between a preassembled electrode interface device 340 that includes the upper and lower sponges 210a, 210b held together by rivets 214a/214b, as represented in FIG. 2.

In the illustrated implementation, it can be seen that the electrode 212 is inserted far enough into the space between the upper and lower sponges 210a, 210b that the entire flat bottom surface of the disk-shaped portion 228 of the electrode 212 is able to contact the inner surface of the lower substantially porous material 210b. In the illustrated implementation, it can also be seen that the rivets 214a/214b are placed far enough away from one another that the electrode 212 can be slid between the upper and lower sponges 210a, 210b.

FIG. 4A to FIG. 4E are bottom views of an electrode interface device (e.g., 340 in FIG. 3A) showing a variety of possible configurations for the lower sponge 210b and the lower rivet heads 220 exposed at the outer surface thereof. Of course, a variety of other configurations are possible as well.

Figure 4B:
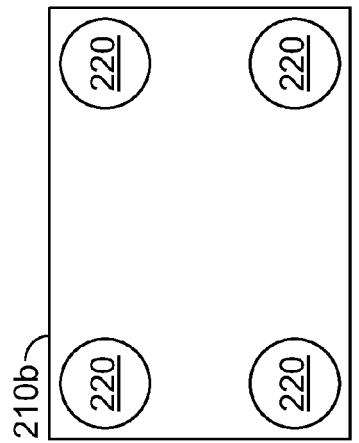
FIGS. 4A to 4E are bottom views of electrode assemblies showing different rivet configurations.
Figure 4E:
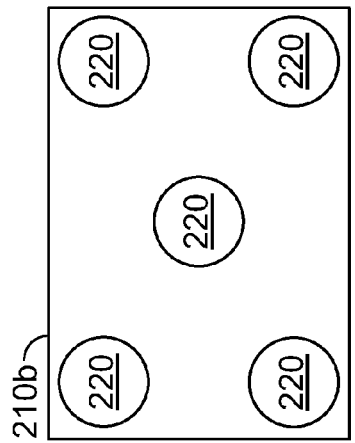
Figure 4C:
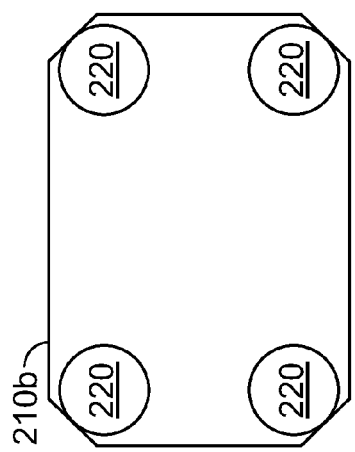
Figure 4A:
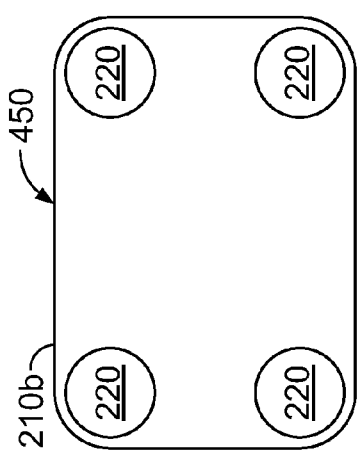

In FIG. 4A, for example, the bottom surface (i.e., the "contact surface") of the lower sponge 210b is substantially rectangular but with rounded corners. In the illustrated implementation, the lower sponge 210b has an edge that extends from the bottom surface (into the page) and defines an outer perimeter of the sponge.

There are four lower rivet heads 220 exposed at the bottom surface of the lower sponge 210b, each rivet head being proximate one of the rounded corners of the bottom surface. In a typical implementation, the exposed rivet heads 220 are relatively close to, but usually not touching or overlapping the closest edge (or corner) of the bottom surface. For example, in some implementations and, as shown in FIG. 4A, the outermost points of the exposed rivets heads are no further from the nearest edge of the bottom surface than approximately 50% of the width of the rivet head. In some implementations, the center of the rivet head is between about 0.5 centimeters and 1.6 centimeters from the nearest edge or edges of the bottom surface of the sponge. In some implementations, the center of the rivet head is between about 0.5 centimeters and 1.6 centimeters from the nearest edge of another rivet, too.

The rivet heads 220 in FIG. 4A are arranged in a substantially symmetrical manner about the bottom surface of the sponge 210b. Other, non-symmetrical arrangements are possible as well.

The configuration in FIG. 4B is similar to the configuration in FIG. 4A except that the sponge 210b in FIG. 4B has a corner at each point where the bottom surface (the "contact surface") and two of the side edges connect to one another. Therefore, the contact surface has four corners and the rivet heads are exposed at the contact surface near each corner.

The configuration in FIG. 4C is similar to the configuration in FIG. 4B except that the corners of the rectangular lower sponge 210b have been cut off along a straight line. Also, the exposed lower rivet heads 220 are very close to or overlapping the cut off straight edges at each corner.

Figure 4D:
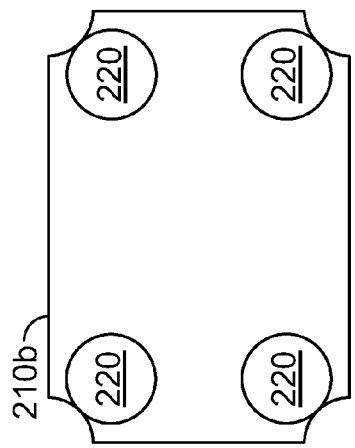

The configuration in FIG. 4D is similar to the configuration in FIG. 4B except that the corners of the rectangular lower sponge 210b have been cut off to form a concave edge at each corner.

The configuration in FIG. 4E is similar to the configuration in FIG. 4B except that there is an additional lower rivet head 220 exposed at a center of the bottom surface of the sponge 210b. This arrangement may be beneficial if, for example, the assembly is particularly long (with length extending in the horizontal direction in FIG. 4E). In such cases, the middle rivet may enhance the structural integrity of the device, particularly across the middle portion of the device.

A number of models were developed to examine how the insulated rivets influence the electrical current flow out of the bottom surface (i.e., the "contact surface") of the bottom sponge in an electrode assembly. Some of the results of the modeling are shown below in Table 1 (below), which cross-references FIGS. 5A-5AB as indicated in the table.

TABLE 1

Figure 5A:
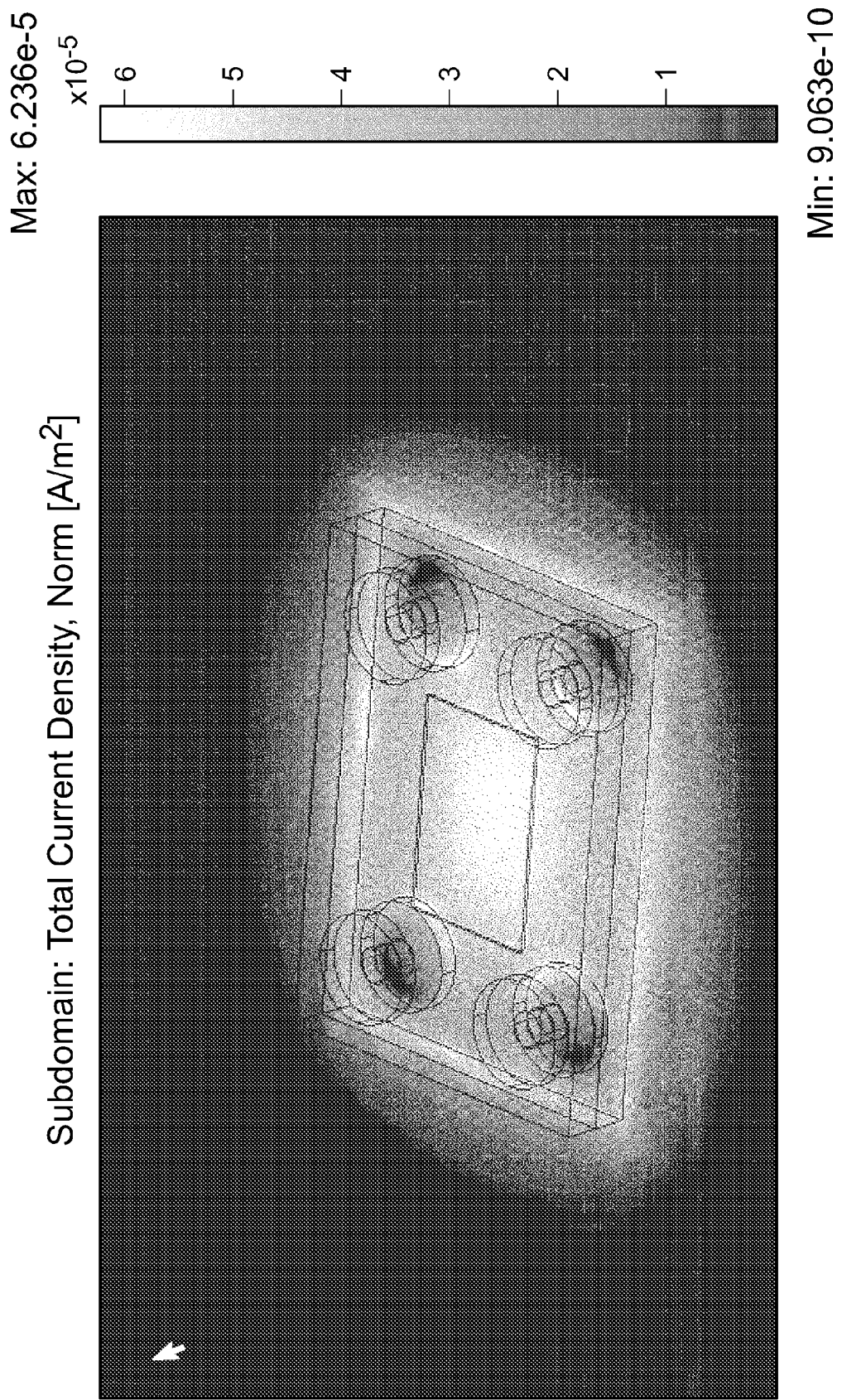
FIGS. 5A to 5AB are representations of computer models of different electrode assembly configurations.
Figure 5B:
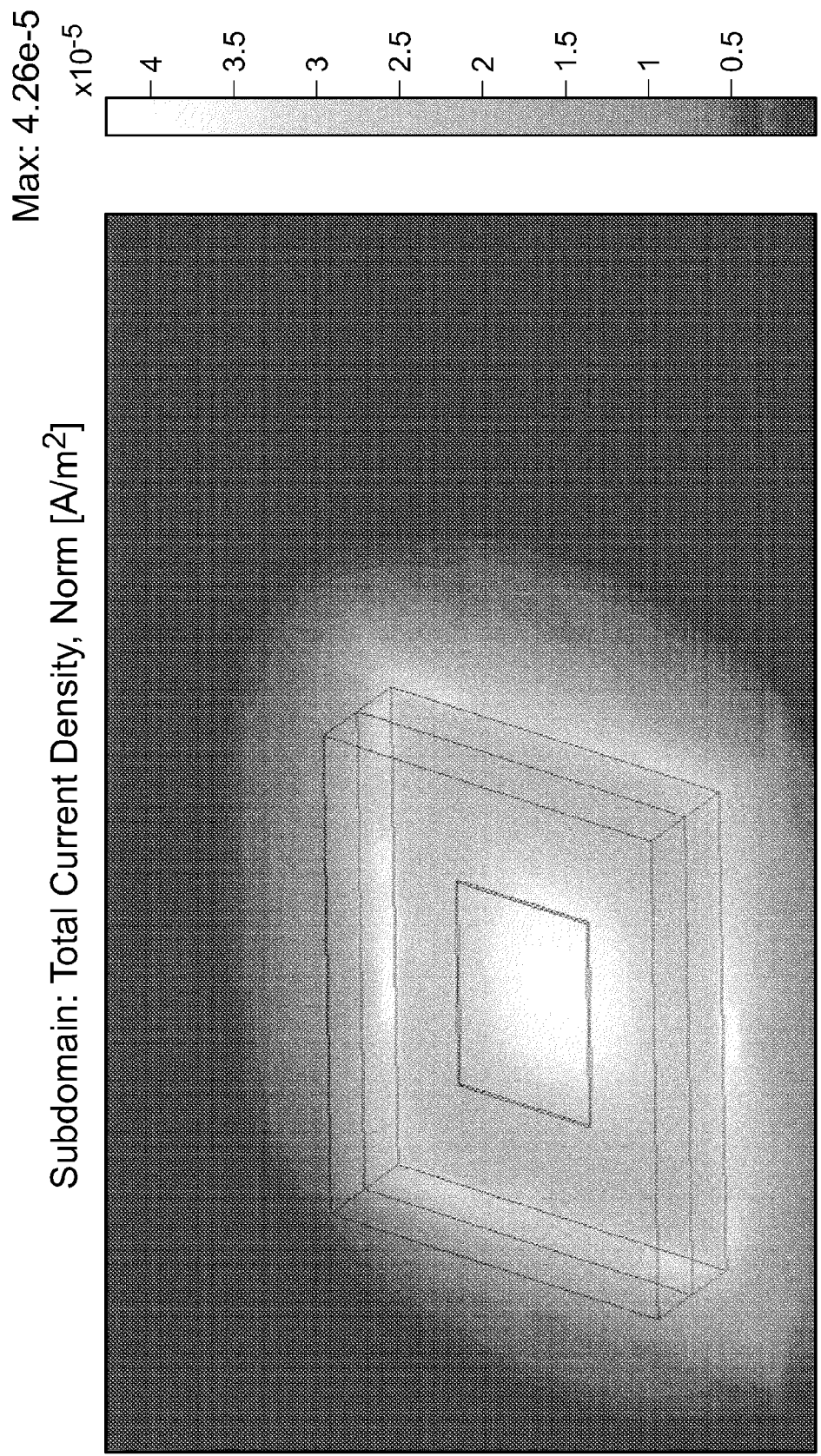
Figure 5C:
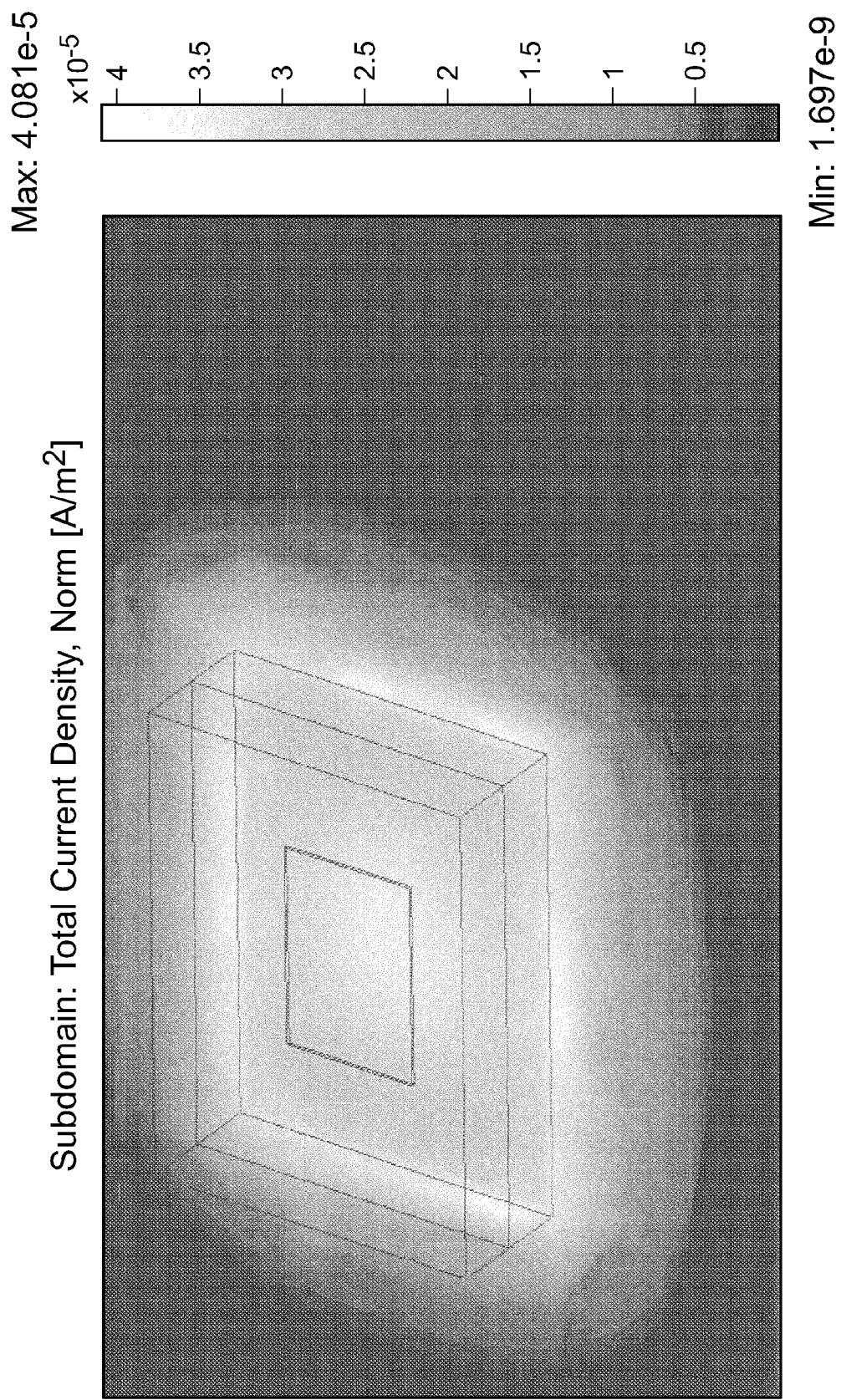
Figure 5D:
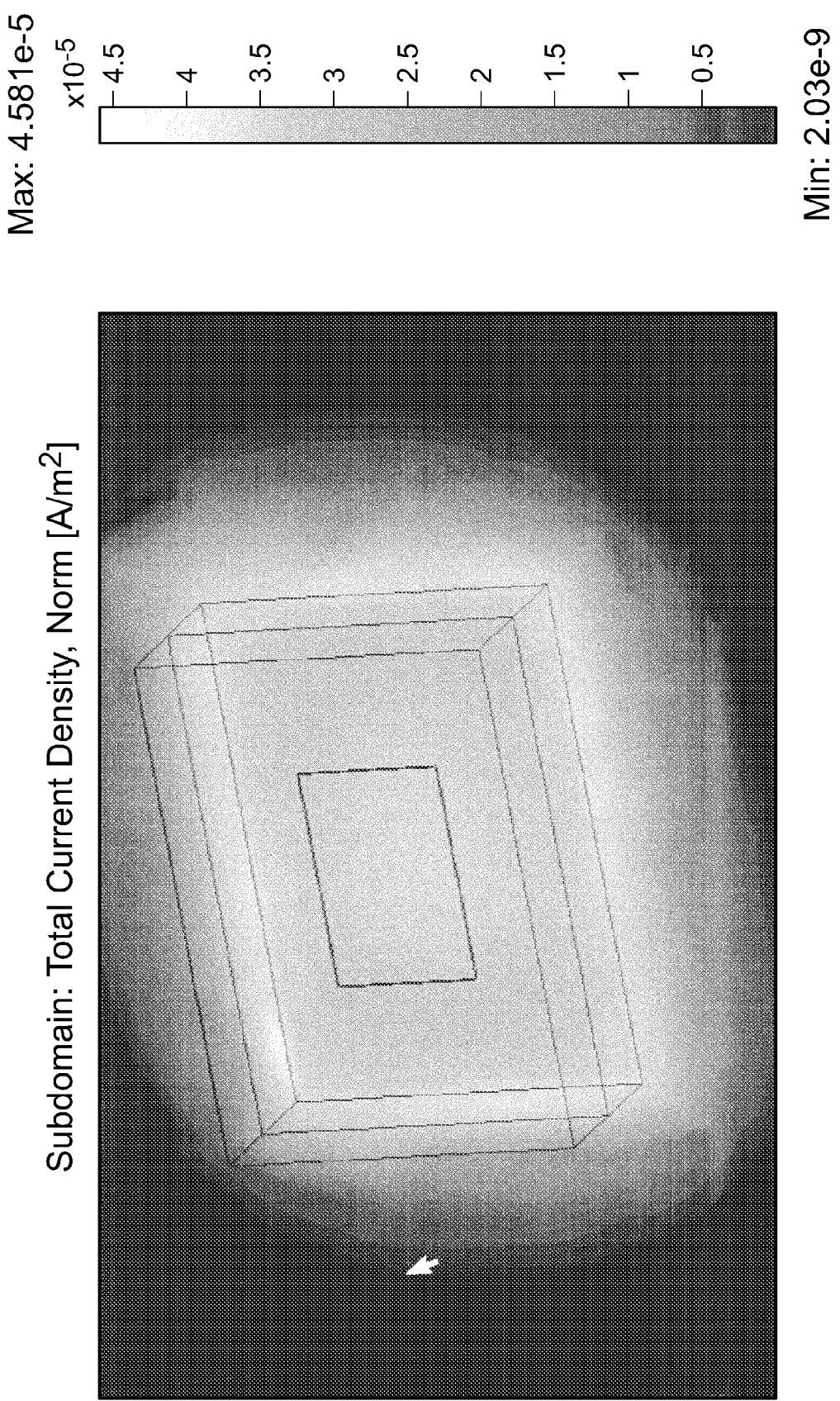
Figure 5E:
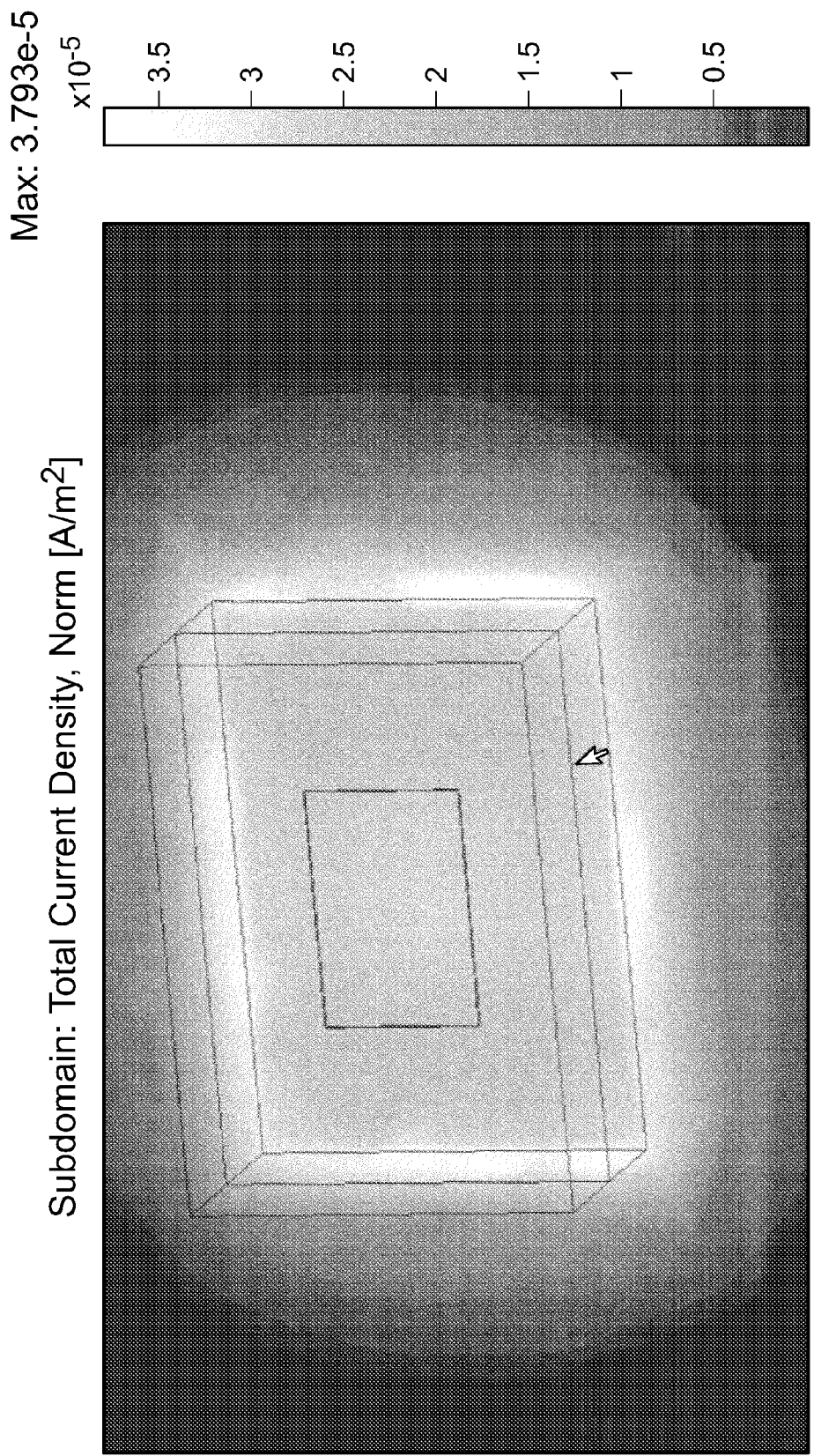
Figure 5F:
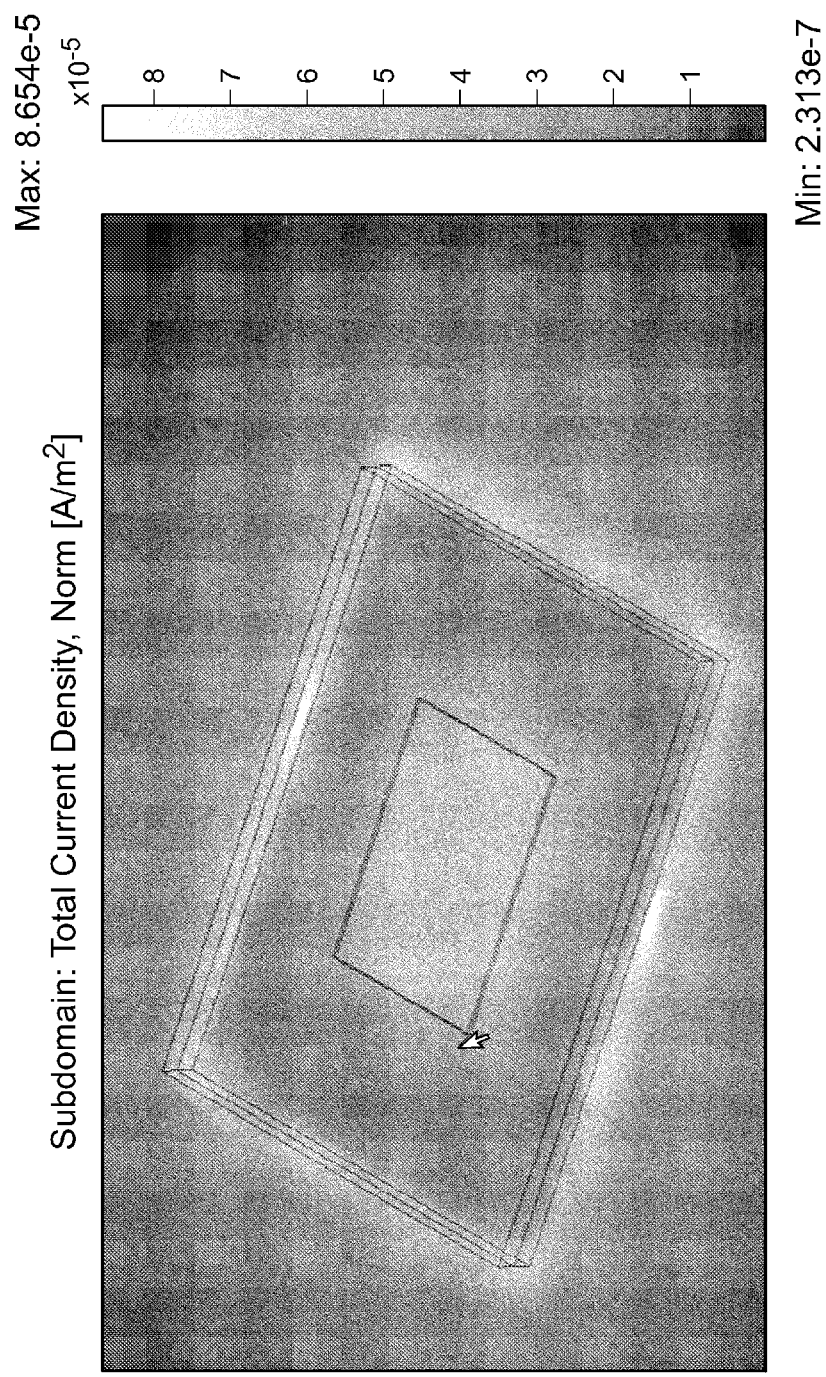

| Name | Max Current Density (A/m^2) | Max Current Density Location | Rivets Axis Distance from Edges (cm) | Sponge Shape | Sponge Thickness (cm) | FIG. |
| --- | --- | --- | --- | --- | --- | --- |
| NoRivets | 5.54E−05 | Center | None | Rectangle | 0.5 | FIG. 5A |
| NoRivets2 | 4.26E−05 | Mostly Center | None | Rectangle | 0.75 | FIG. 5B |
| NoRivets3 | 4.08E−05 | Center/Edge | None | Rectangle | 1 | FIG. 5C |
| NoRivets4 | 4.58E−05 | Mostly Edge | None | Rectangle | 1.25 | FIG. 5D |
| NoRivets5 | 3.79E−05 | Edge | None | Rectangle | 1.5 | FIG. 5E |
| LayeredNoRivets | 8.65E−05 | Center/Edge | None | Rectangle | 0.25 | FIG. 5F |

TABLE 1-continued

Figure 5G:
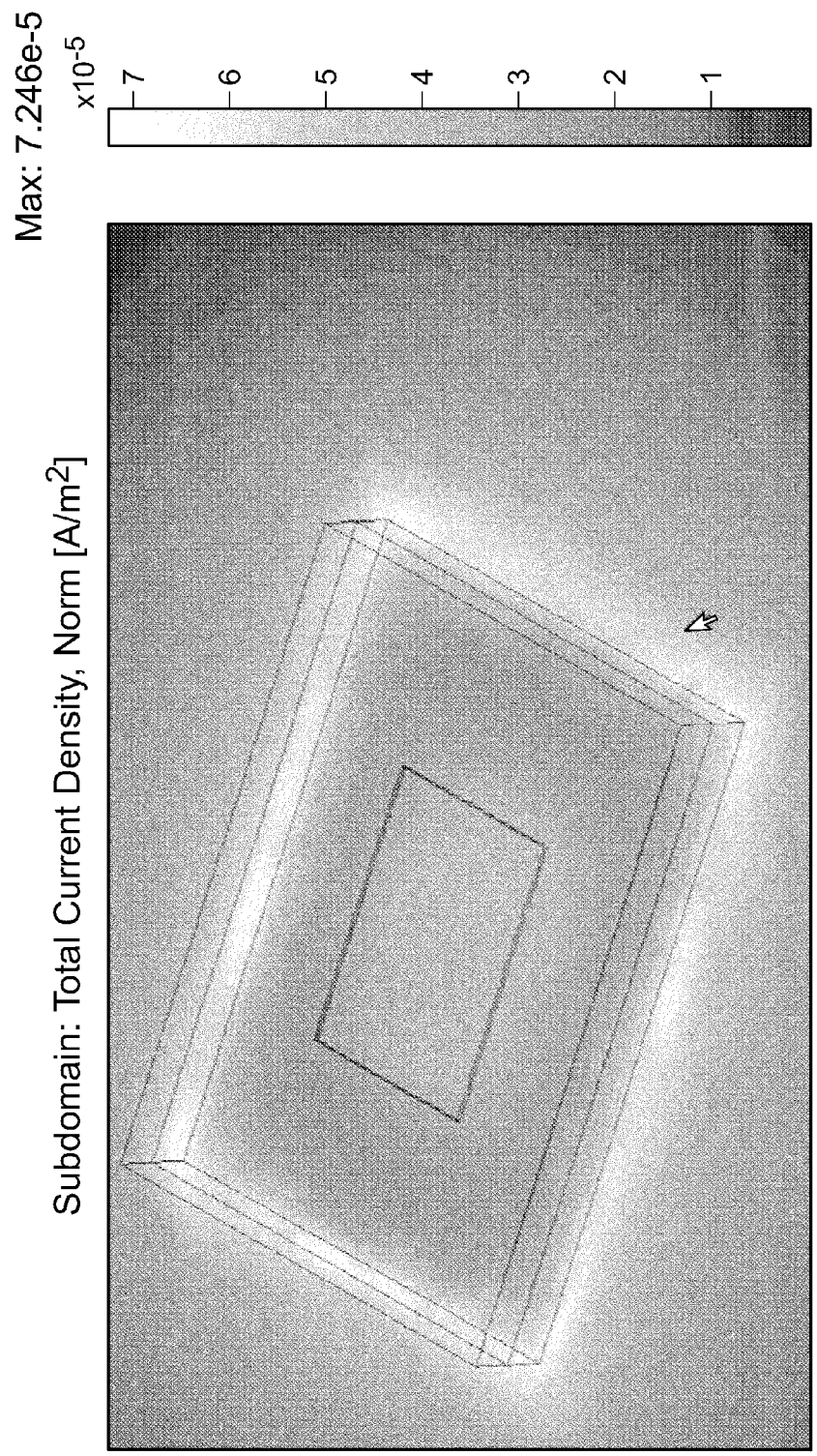
Figure 5H:
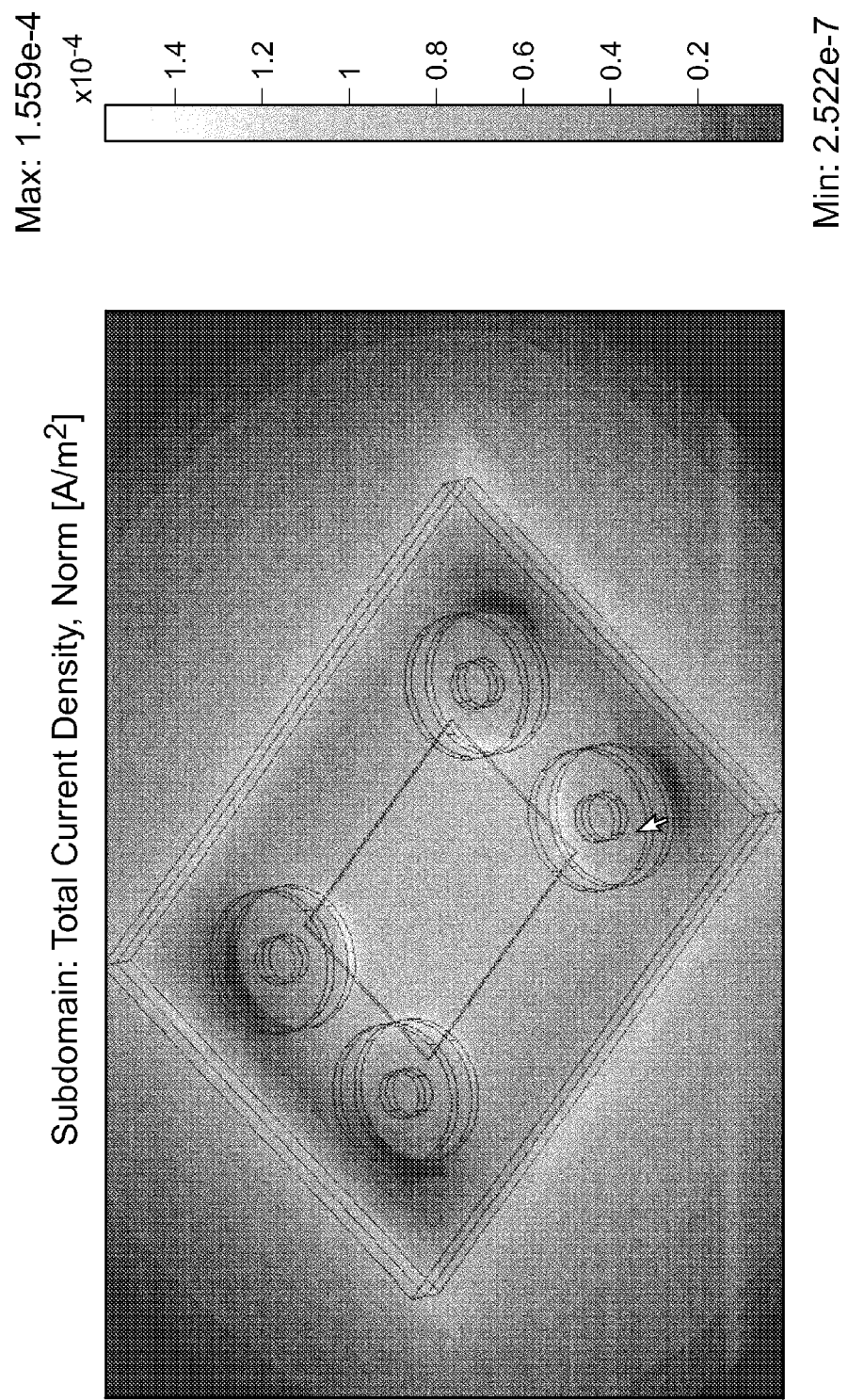
Figure 5I:
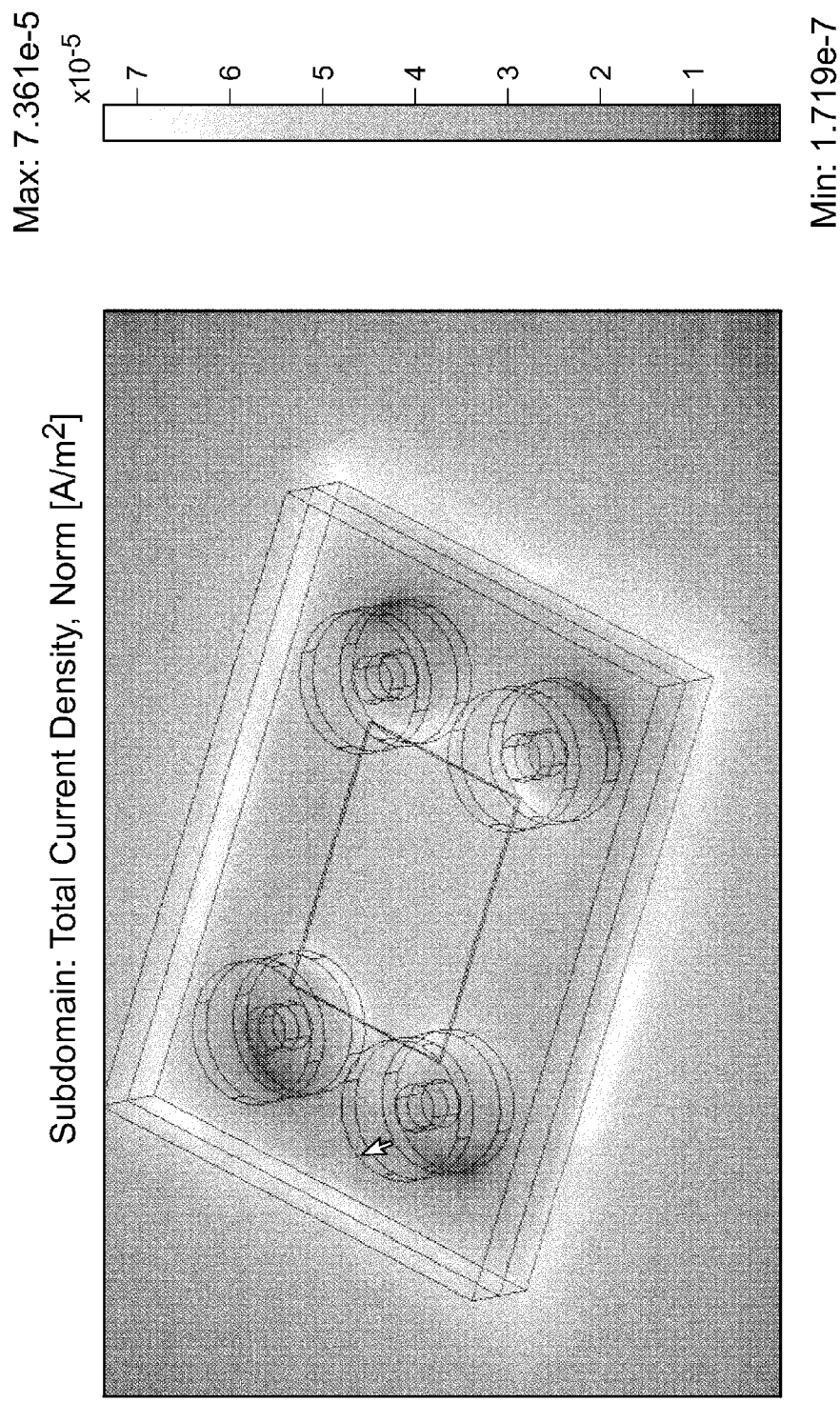
Figure 5J:
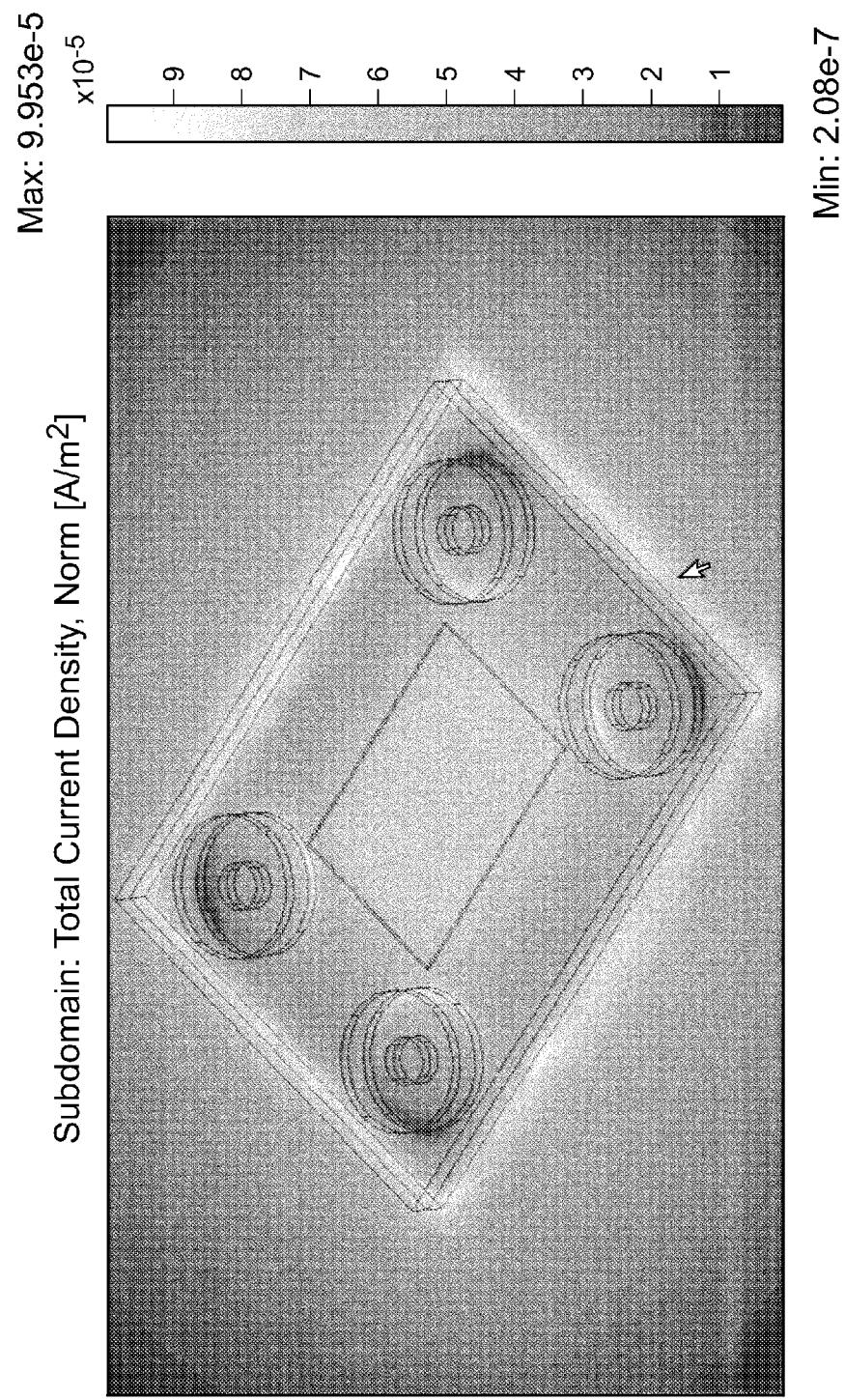
Figure 5K:
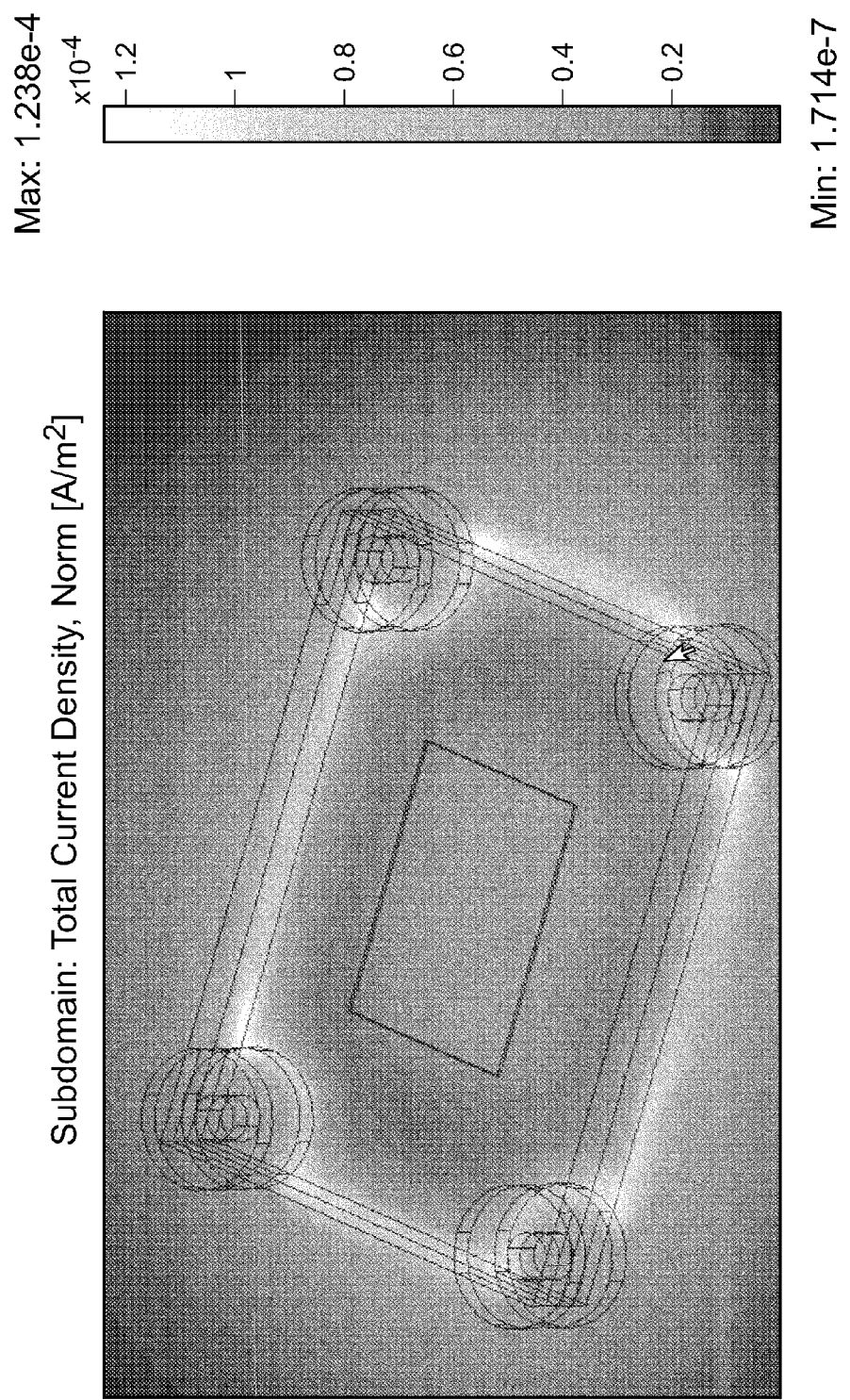
Figure 5L:
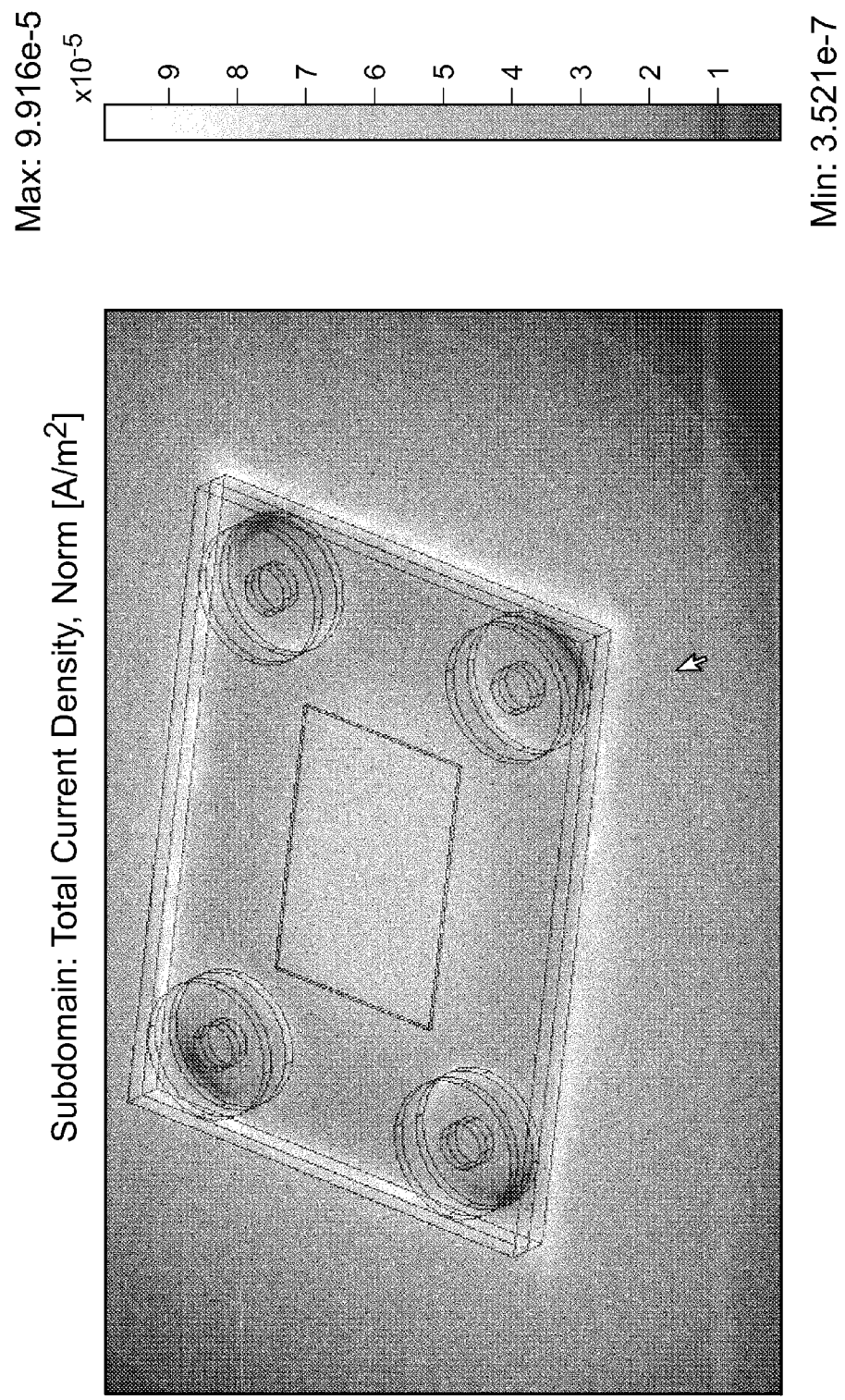
Figure 5M:
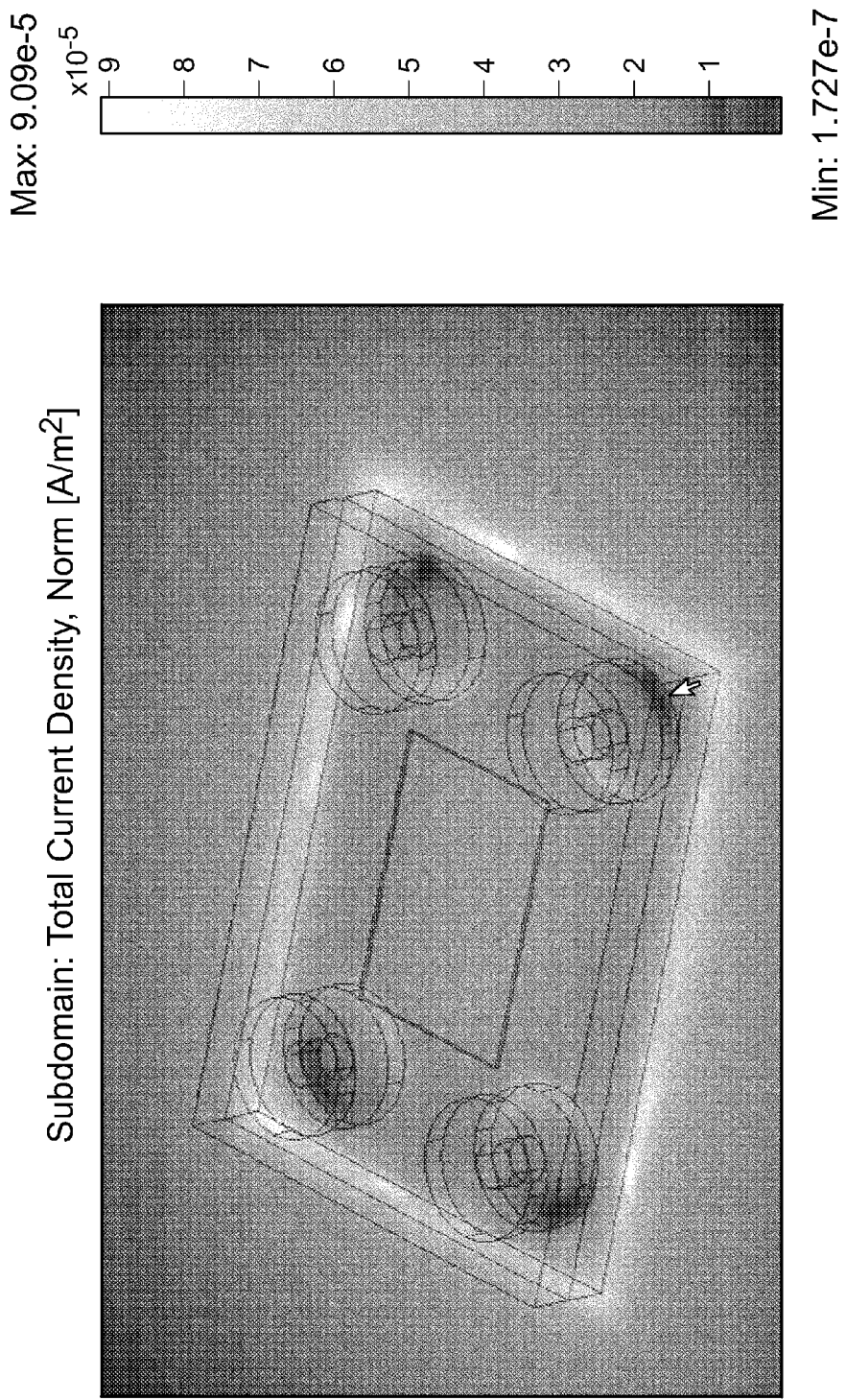
Figure 5N:
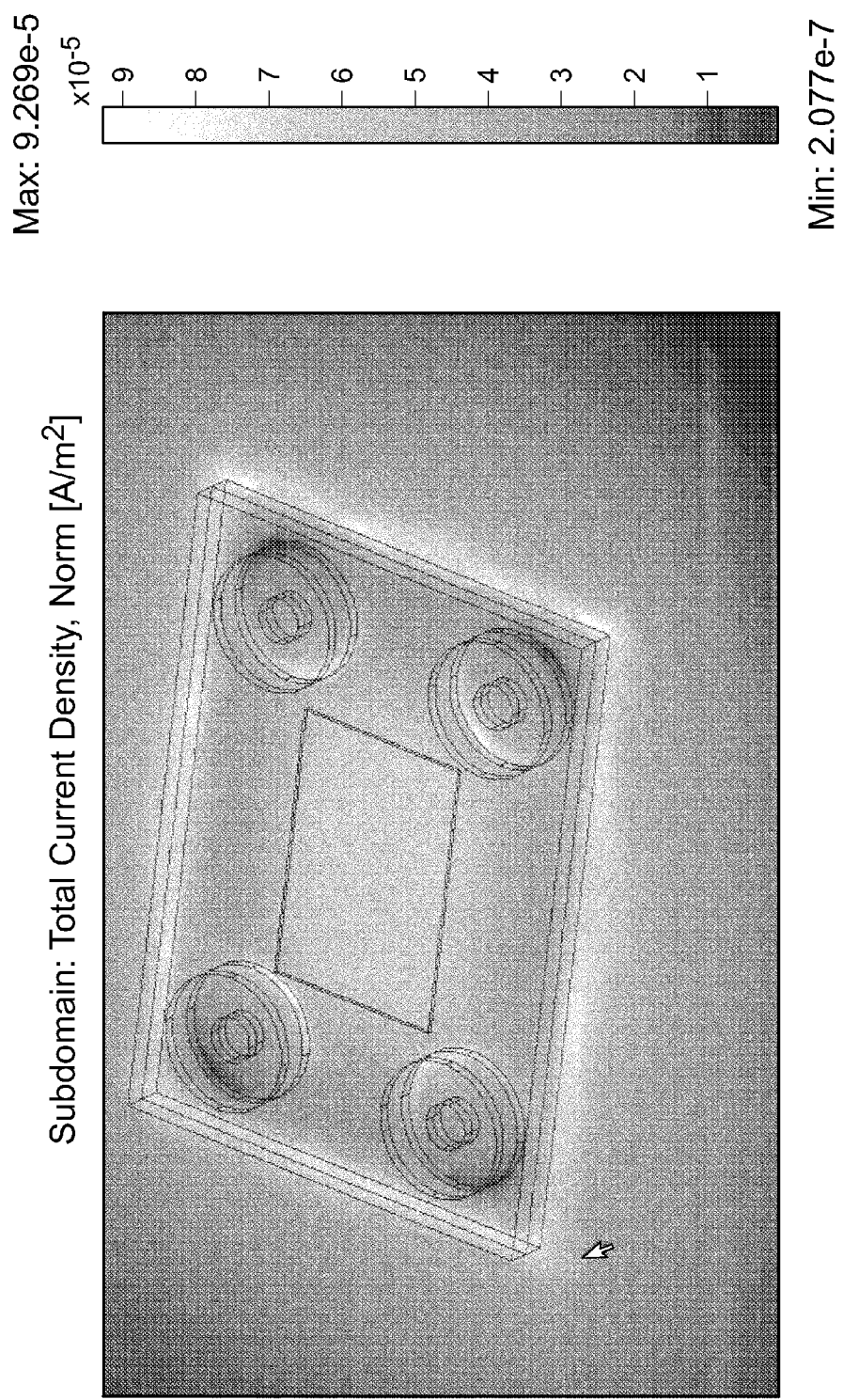
Figure 5O:
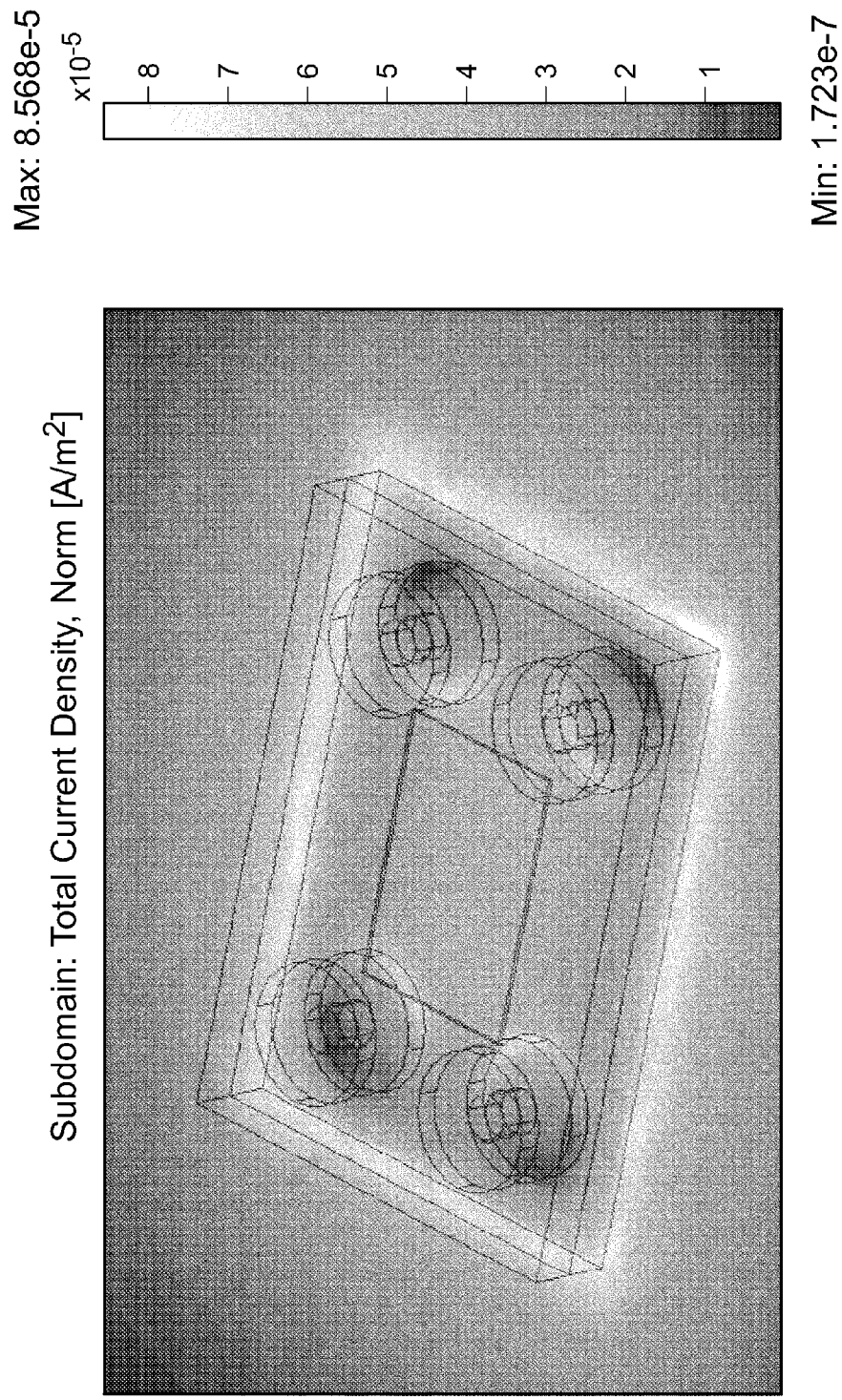
Figure 5P:
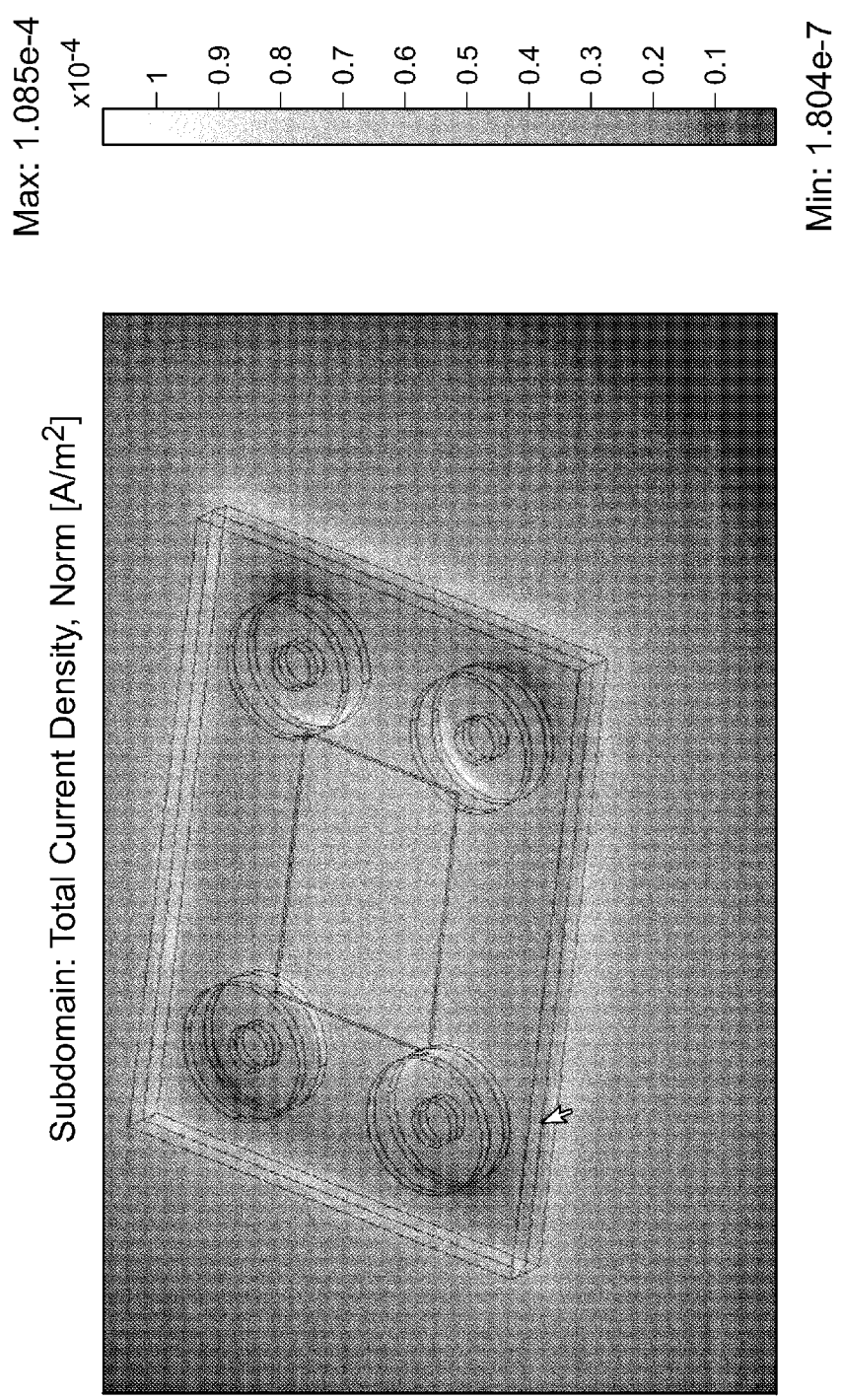
Figure 5Q:
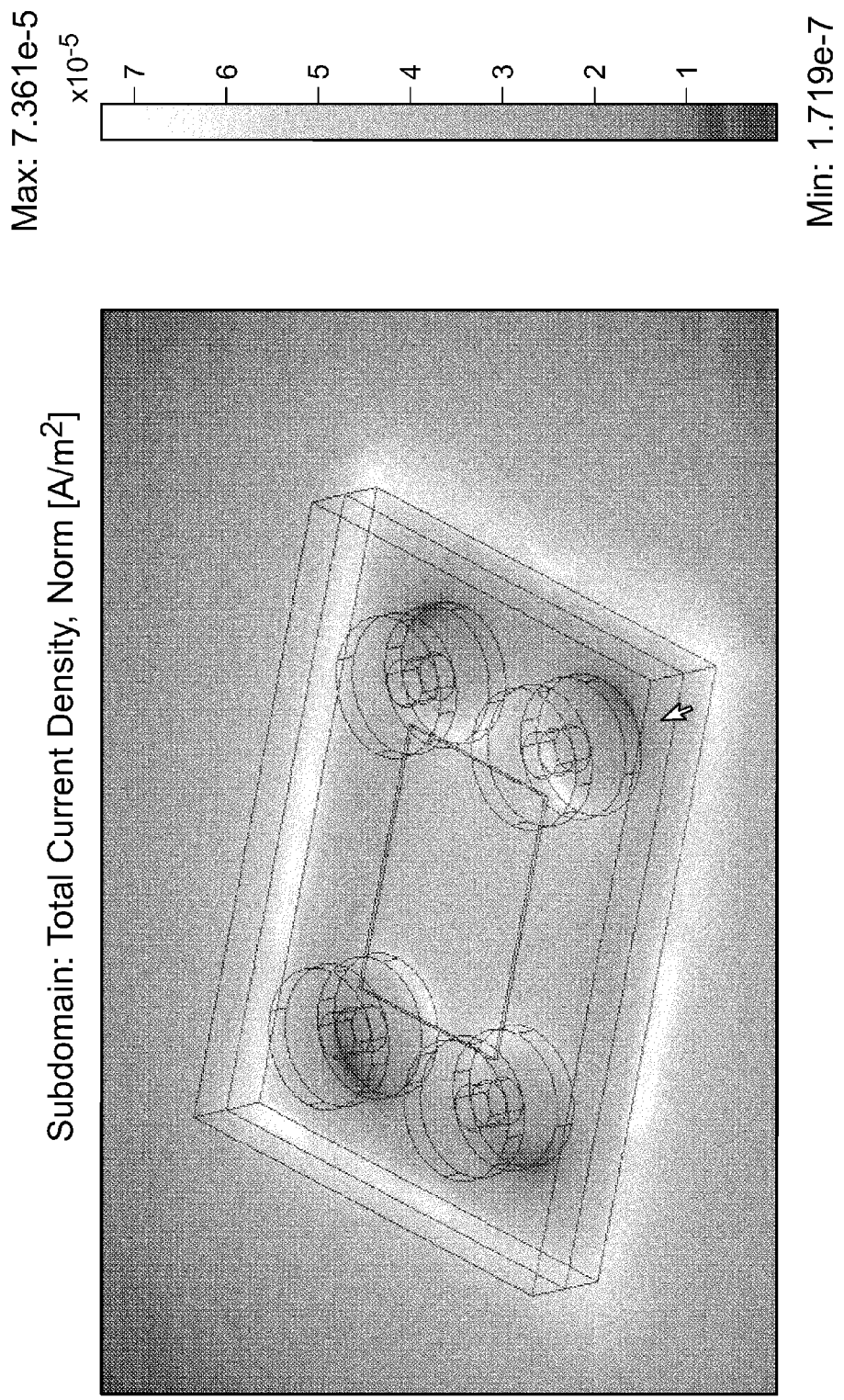
Figure 5R:
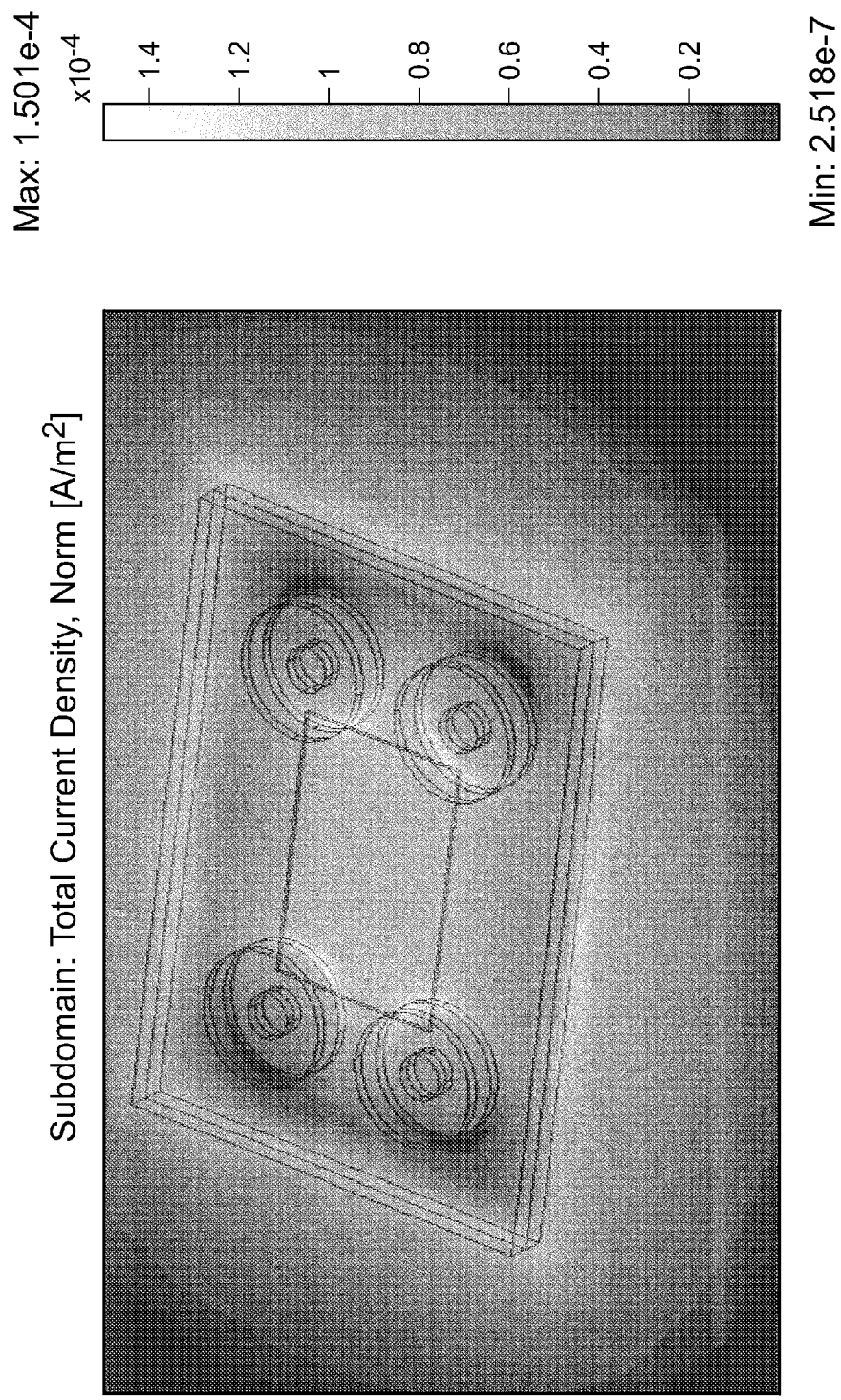
Figure 5S:
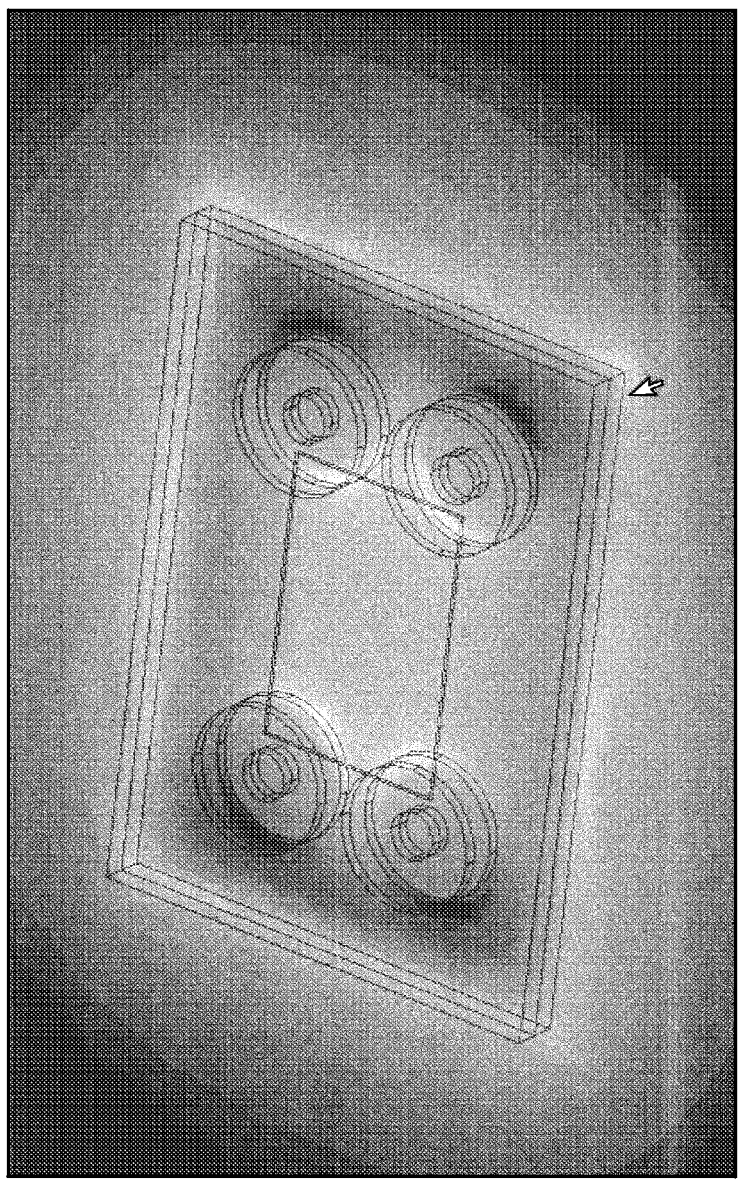
Figure 5T:
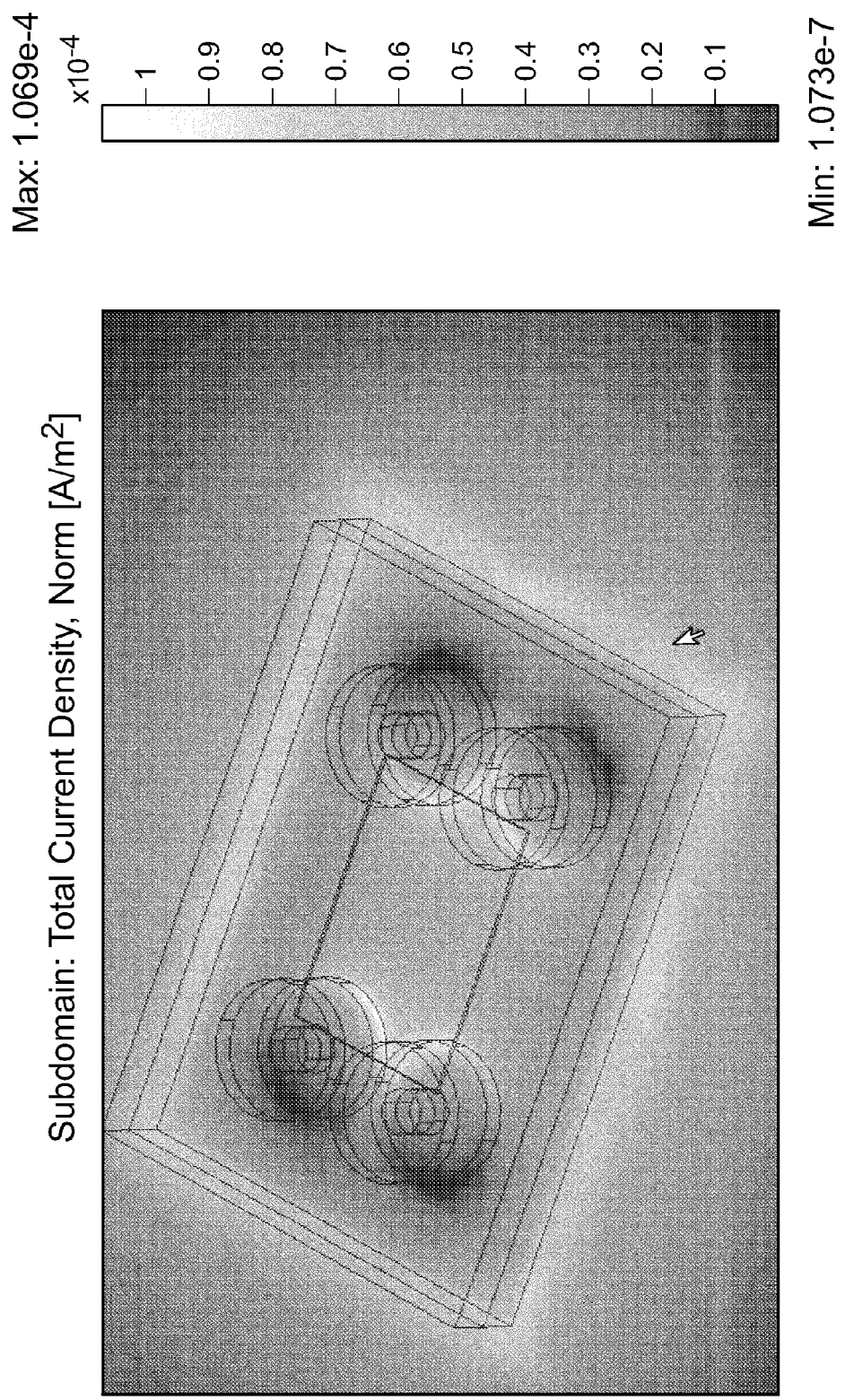
Figure 5U:
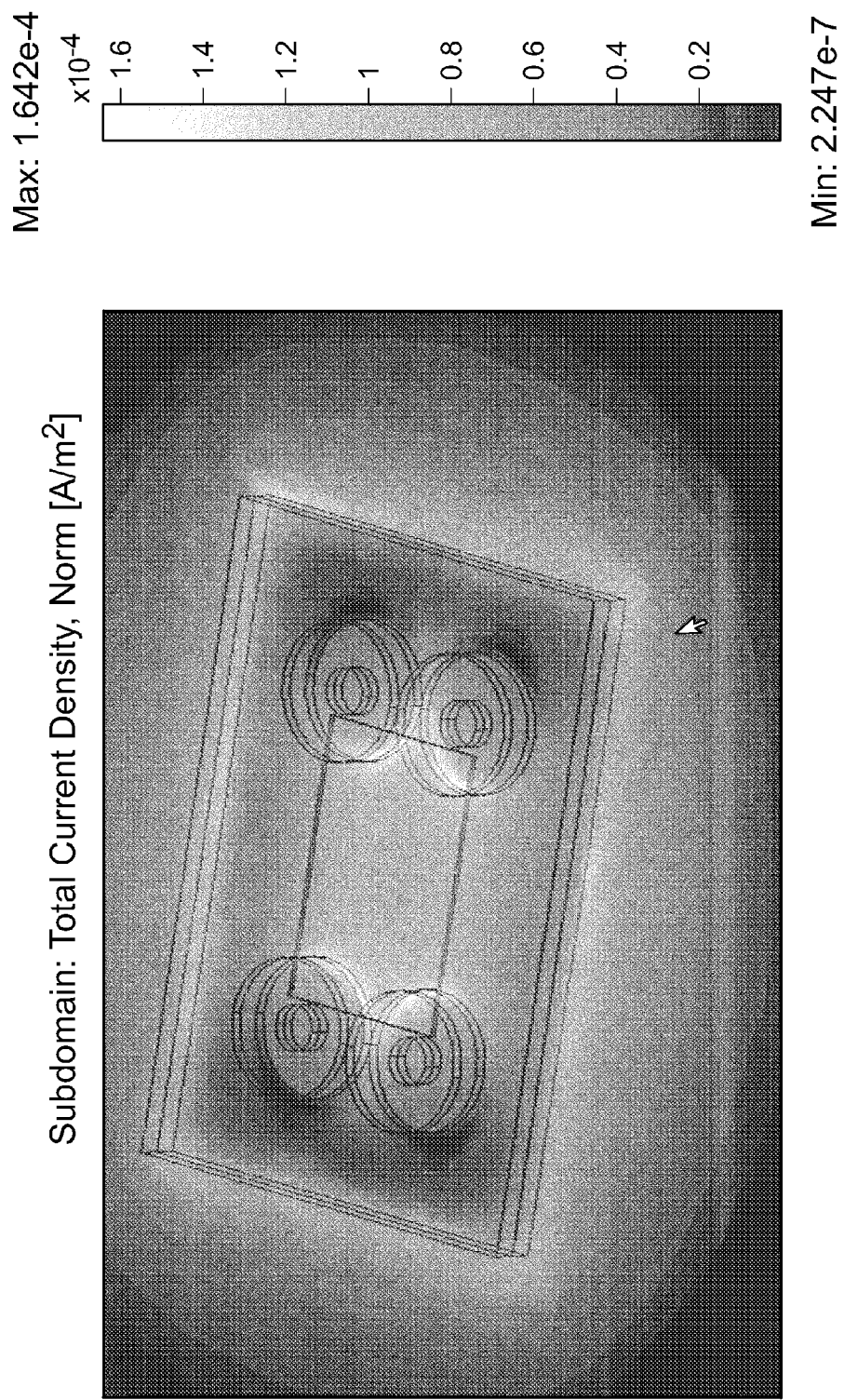
Figure 5V:
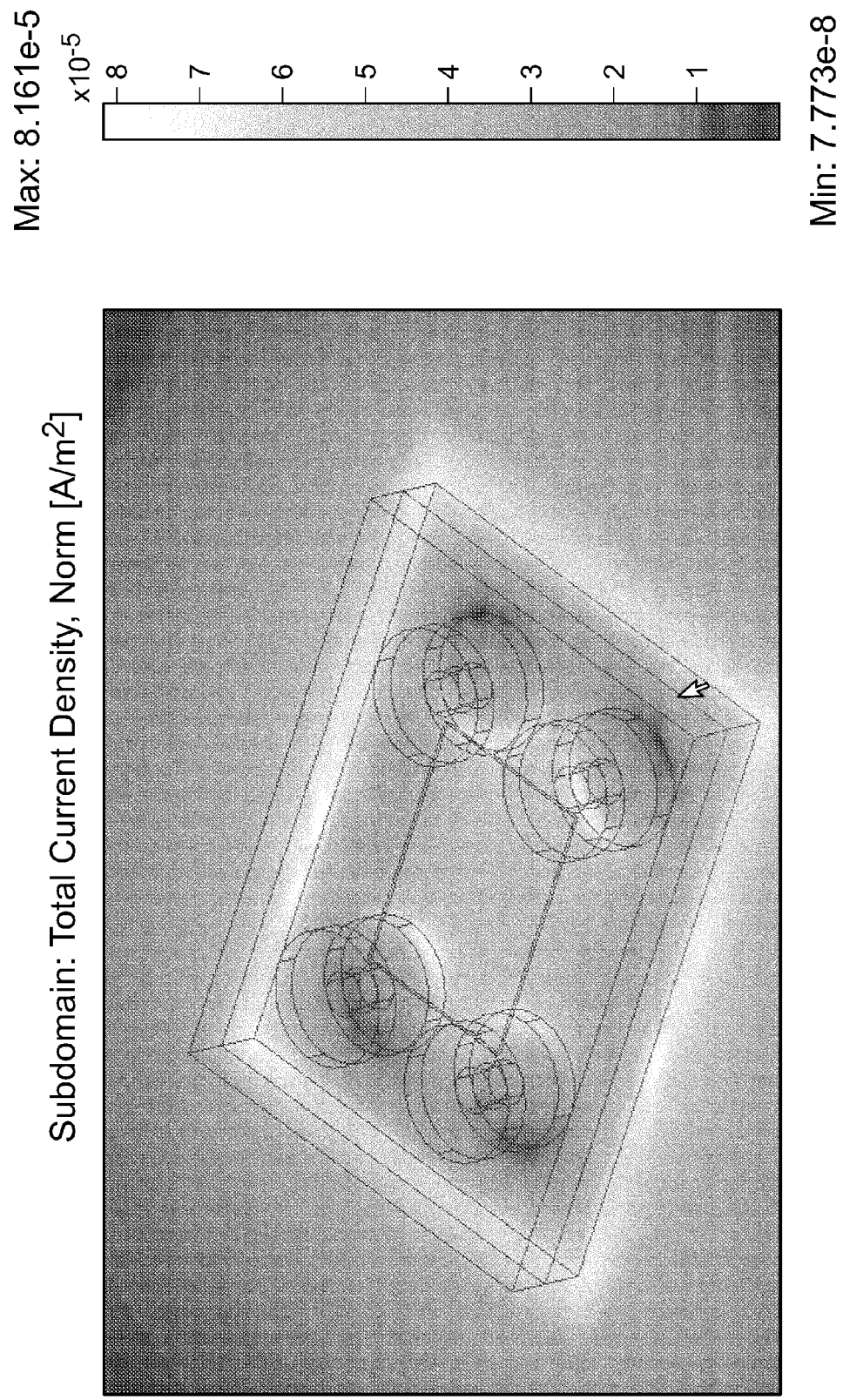
Figure 5W:
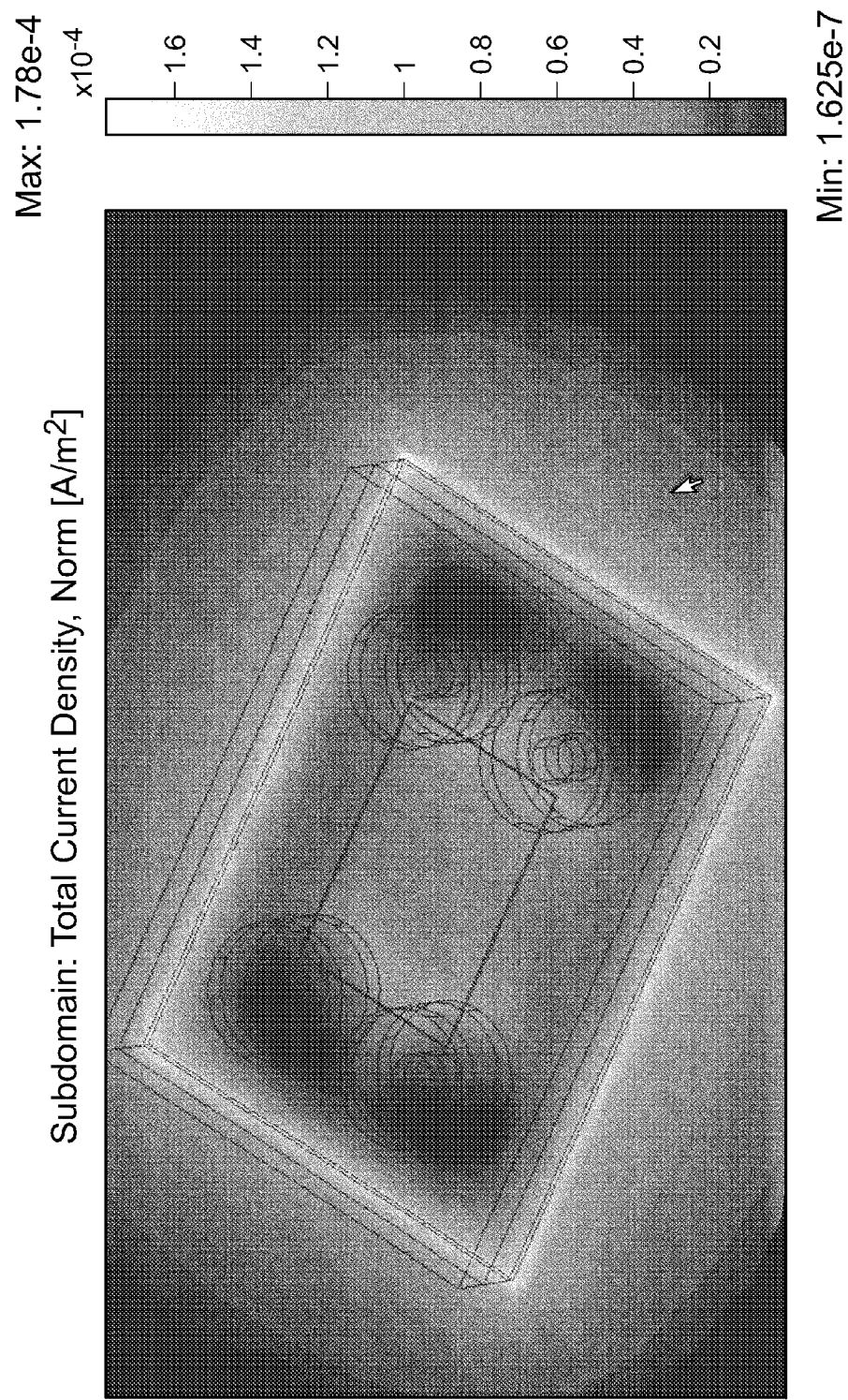
Figure 5X:
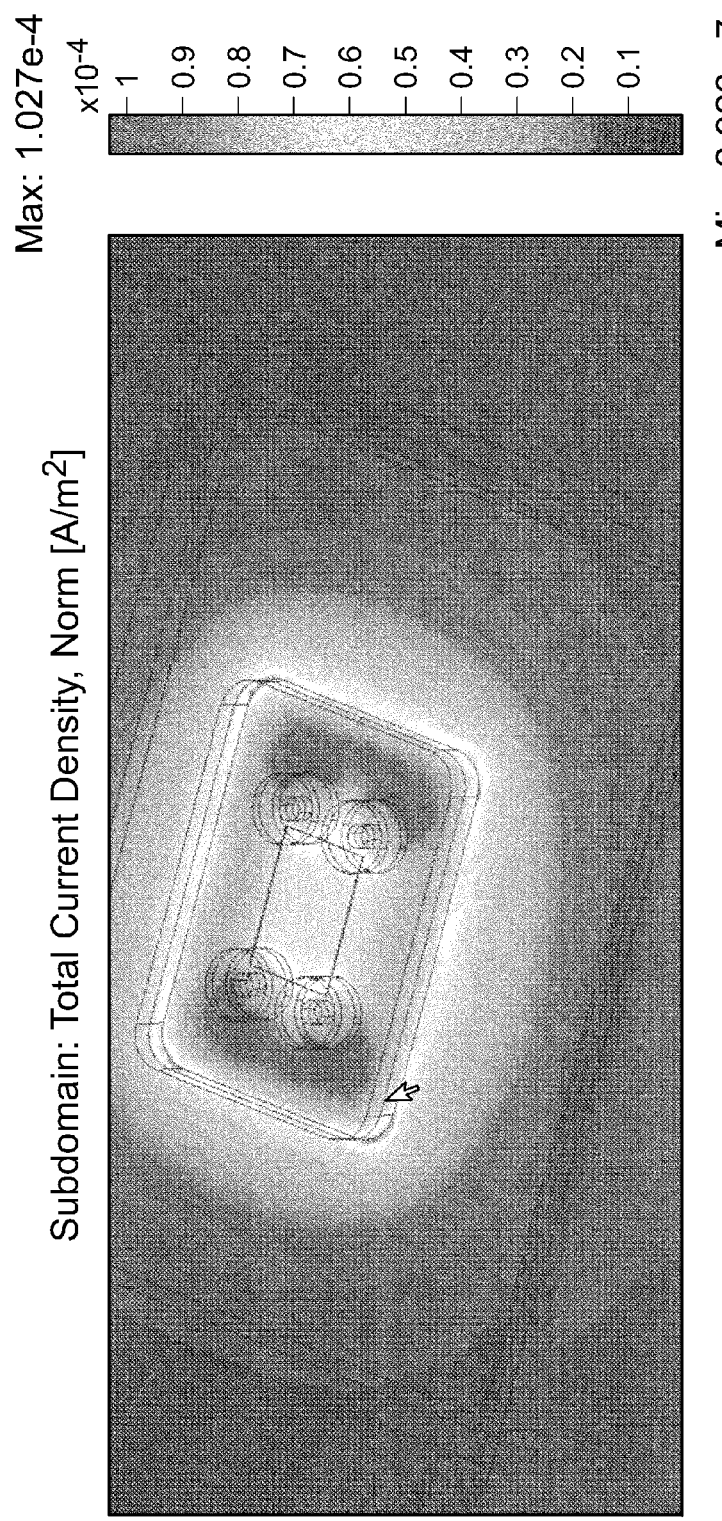
Figure 5Y:
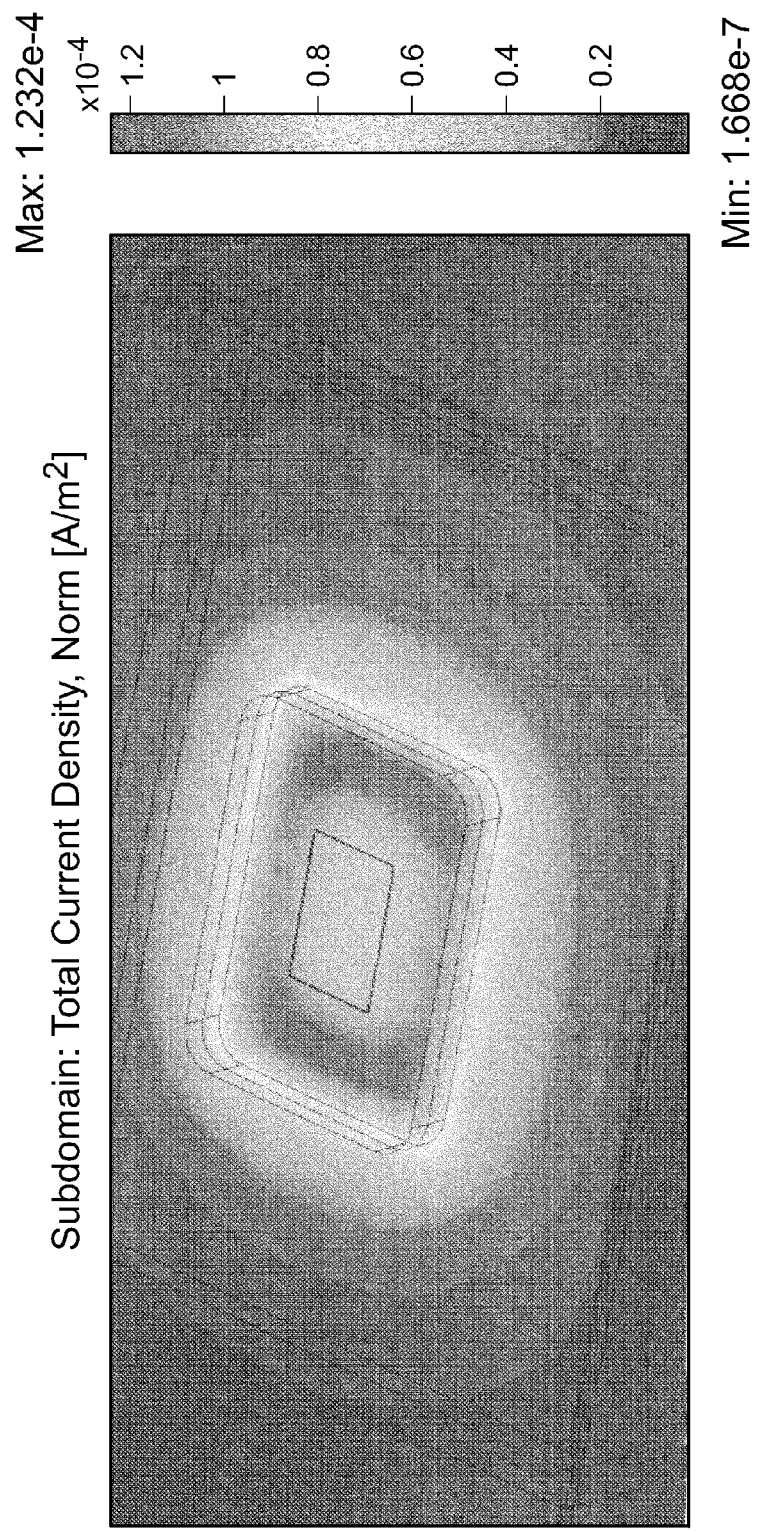
Figure 5Z:
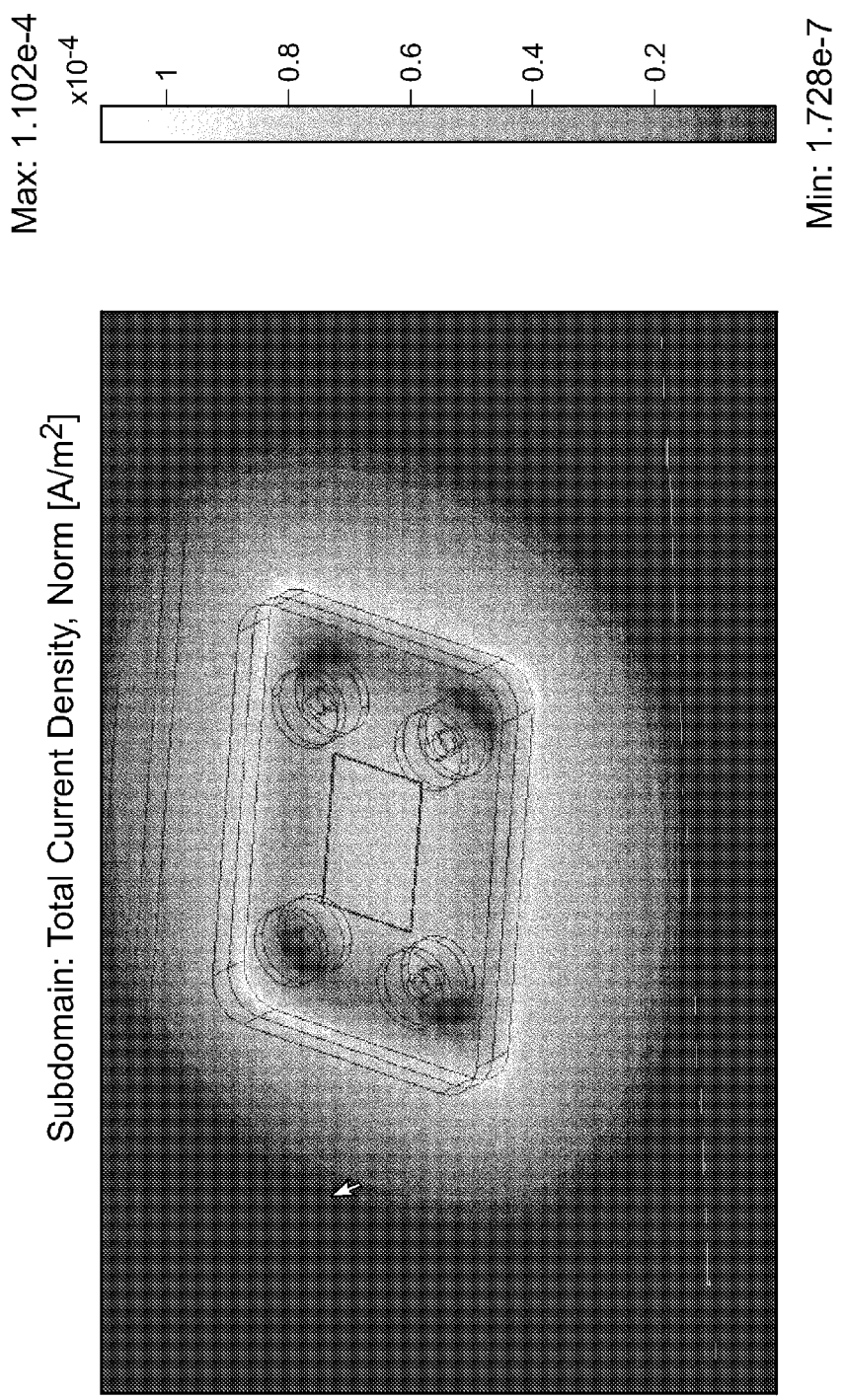
Figure 5A:
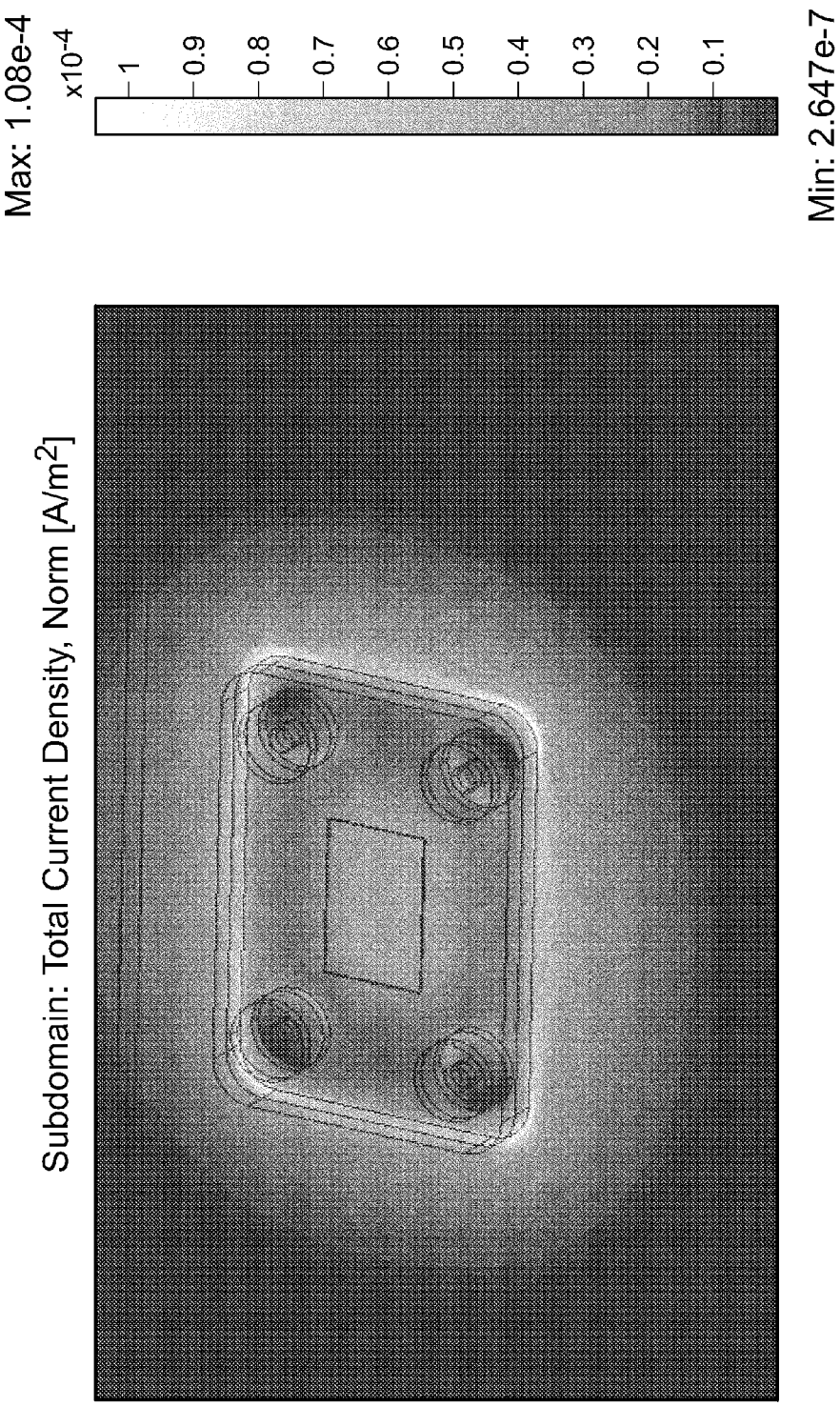
Figure 5A:
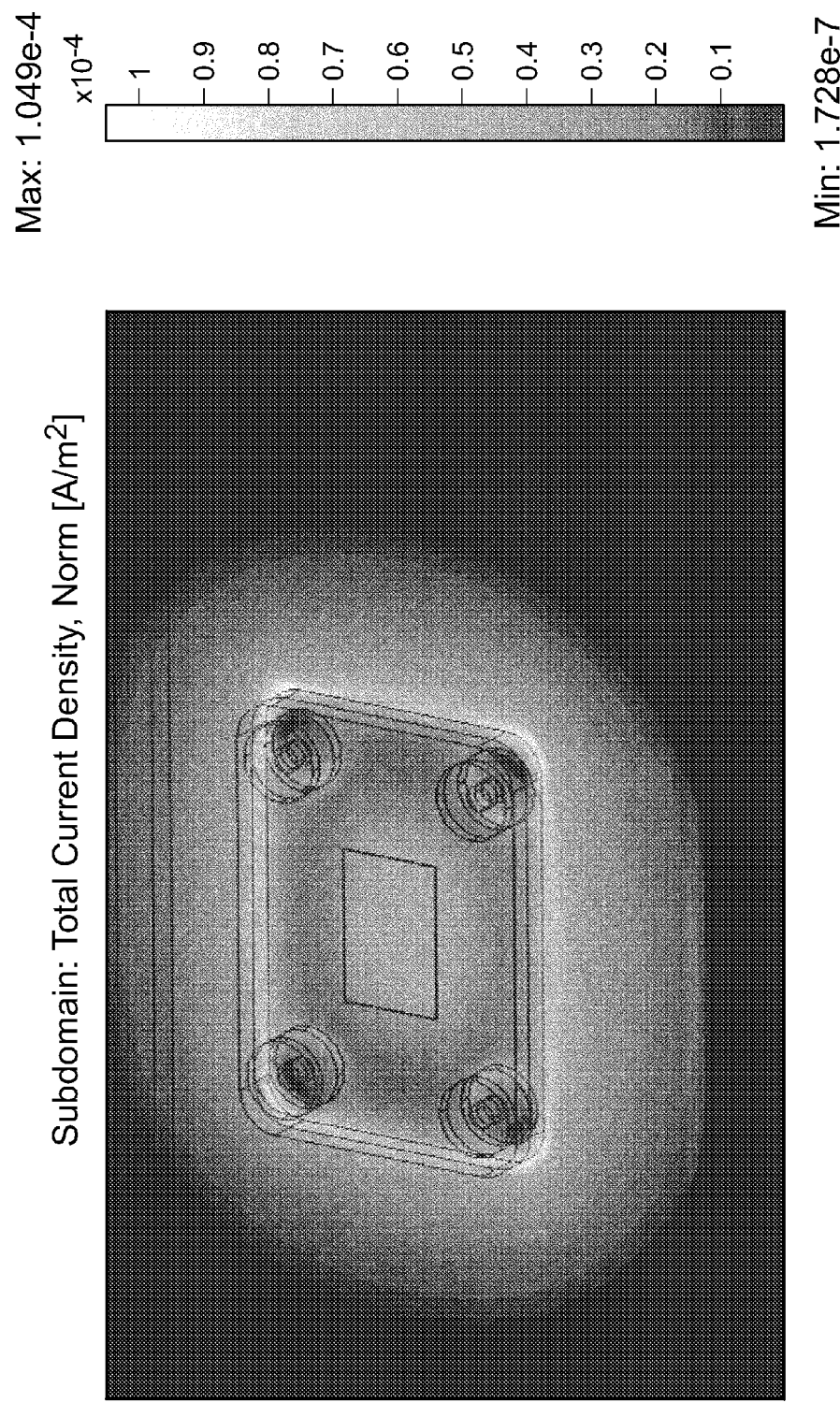

| Name | Max Current Density (A/m^2) | Max Current Density Location | Rivets Axis Distance from Edges (cm) | Sponge Shape | Sponge Thickness (cm) | FIG. |
|---|---|---|---|---|---|---|
| LayeredNoRivets2 | 7.25E−05 | Edge | None | Rectangle | 0.5 | FIG. 5G |
| LayeredRivets | 1.56E−04 | Rivets | 1.5 | Rectangle | 0.25 | FIG. 5H |
| LayeredRivets2 | 7.36E−05 | Edges/Rivets | 1.5 | Rectangle | 0.5 | FIG. 5I |
| LayeredRivets3 | 9.95E−05 | Edges/Rivets | 1.1 | Rectangle | 0.25 | FIG. 5J |
| LayeredRivets4 | 9.07E−05 | Edges/Rivets | 1.1 | Rectangle | 0.5 | FIG. 5K |
| LayeredRivets5 | 1.24E−04 | Edges/Rivets | On Corners | Rectangle | 0.5 | |
| LayeredRivets6 | 1.76E−04 | Center/Edge/Rivets | On Corners | Rectangle | 0.25 | |
| LayeredRivets7 | 1.07E−04 | Edge | 0.9 | Rectangle | 0.5 | |
| LayeredRivets8 | 9.91E−05 | Center/Edge/Rivets | 0.9 | Rectangle | 0.25 | FIG. 5L |
| LayeredRivets9 | 9.09E−05 | Edge | 1.1 | Rectangle | 0.5 | FIG. 5M |
| LayeredRivets10 | 9.27E−05 | Center/Edge/Rivets | 1.1 | Rectangle | 0.25 | FIG. 5N |
| LayeredRivets11 | 8.57E−05 | Edges/Rivets | 1.3 | Rectangle | 0.5 | FIG. 5O |
| LayeredRivets12 | 1.09E−04 | Rivets | 1.3 | Rectangle | 0.25 | FIG. 5P |
| LayeredRivets13 | 7.36E−05 | Edges/Rivets | 1.5 | Rectangle | 0.5 | FIG. 5Q |
| LayeredRivets14 | 1.50E−04 | Rivets | 1.5 | Rectangle | 0.25 | FIG. 5R |
| LayeredRivets15 | 7.24E−05 | Edges/Rivets | 1.6 | Rectangle | 0.5 | |
| LayeredRivets16 | 1.59E−04 | Rivets | 1.6 | Rectangle | 0.25 | FIG. 5S |
| LayeredRivets17 | 1.07E−04 | Rivets | 1.7 | Rectangle | 0.5 | FIG. 5T |
| LayeredRivets18 | 1.64E−04 | Rivets | 1.7 | Rectangle | 0.25 | FIG. 5U |
| LayeredRivets19 | 8.16E−05 | Edges/Rivets | x: 1.6, z: 1.5 | Rectangle | 0.5 | FIG. 5V |
| LayeredRivets20 | 1.78E−04 | Edges of saline layer | 1.6 | Rectangle | 0.5 | FIG. 5W |
| RoundLayered NoRivets | 1.23E−04 | Edge | None | Rounded Edges | 0.5 | FIG. 5X |
| RoundLayered Rivets1 | 1.03E−04 | Corners | 1.6 | Rounded Edges | 0.5 | FIG. 5Y |
| RoundLayered Rivets2 | 1.10E−04 | Corners | 1.1 | Rounded Edges | 0.5 | FIG. 5Z |
| RoundLayered Rivets3 | 1.08E−04 | Corners | 0.6 | Rounded Edges | 0.5 | FIG. 5AA |
| RoundLayered Rivets4 | 1.05E−04 | Corners | 0.4 | Rounded Edges | 0.5 | FIG. 5AB |

The total current being delivered by the modeled electrode assembly was about 1 milliamp in each instance. For each model, Table 1 indicates a name assigned to that model, the maximum simulated current density at any given spot on the contact surface of the corresponding simulated electrode assembly, the location of the maximum current density, the distance in centimeters from the rivet's axis to the closest edge of the sponge, the sponge shape, the sponge thickness and the corresponding one of FIGS. 5A-5AB, which provides a visual representation of the modeled electrode assembly.

Each of FIGS. 5A-5AB show visual representations of modeled electrode assemblies. Each modeled electrode assembly shows sponges and an electrode (represented by a square shape approximately centrally located relative to the sponges). Also, some of the visual representations also show rivets.

Each of the visual representations include shading of varying degree that represents different current densities passing through the bottom surface of the lower electrode into a patient. A scale is provided at the right side of each figure identifying the current density that each different shade in the model represents. In FIG. 5A, for example, the scale on the right of the figure goes from $9.063 \times 10^{-10}$ A/m$^2$ up to $6.236 \times 10^{-5}$ A/m$^2$. A visual inspection of the modeled electrode assembly reveals that the highest current density according to this model can be expected around the center of the bottom sponge, whereas the lowest current density occurs at the rivets, which are non-conductive.

There are a several noteworthy observations, some of which can find support in the data in Table 1 and in FIGS. 5A-5AB.

For example, in general the thicker the sponge, probably up to some limit, the greater the likelihood is that electrical current emanating from the electrode will extend out near the edges of the sponge and pass into the patient near the sponge's perimeter. In some implementations, therefore, it appears possible to control or at least influence the current density at different points along the contact surface of the electrode assembly by modifying the thickness of the bottom sponge in the assembly. In some implementations, the thickness of the bottom sponge is between about 0.5 centimeters and 2 centimeters.

The resistivity or salinity of the sponge influences current dispersion in a similar manner to sponge thickness. High resistivity sponge properties act similar to thinner sponges, while low resistivity sponges act similar to thicker sponges. In this way, sponge with a lower thickness and lower resistivity can function like a sponge with higher thickness and higher resistivity. Thus decreasing resistivity may increase performance. In some implementations, decreasing resistivity to a still lower value may be undesired as it results in an extreme concentration of current at sponge edges.

The properties of the sponge, including resistivity, may be controlled in a number of ways. For example, the salt content of the electrolyte in the sponge can be increased to decrease resistivity or decreased to increase resistivity. The primary anion salt may be sodium or calcium, or a combination of the two ions. Salinity close to saline or cerebrospinal fluid is preferred but may be increased or decreased by 50%. The porosity of the sponge may be controlled. Increasing pore size or the density of pores will typically increase conductivity of the sponge. Porosity factors effecting resistivity may be compensated for by adjusting salinity as described.

Additionally, depending on other parameters, the electrically insulated rivets may improve the distribution of electrical current flowing out of the contact surface of the sponge by reducing the maximum current density that occurs at the contact surface and/or by facilitating a more even distribution of electrical current density across the contact surface.

Moreover, in thinner sponges (e.g., 0.25 centimeters thick), current from a centrally disposed electrode tends to pass through the bottom surface of the sponge mostly near the center of the sponge, with very little to no current passing through the contact surface near the outer perimeter of the surface. In those instances, adding rivets near the edges of the sponge seems to draw the current out from the middle and toward the perimetral edges of the sponge. In some instances, this can result in a reduction in maximum current density through the contact surface at any one point and can result in a more even distribution of current through the contact surface.

On the other hand, in thicker sponges (e.g., 0.5 centimeters thick), current tends to reach the perimetral edges of the sponge somewhat naturally without the insulating rivets. In those instances, adding insulating rivets appears to be able to block some of the current flowing toward the perimetral edges and directing it out of the sponge in a more centrally located spot on the contact surface. In some instances, this can result in a reduction in maximum current density through the contact surface at any one point and can result in a more even distribution of current through the contact surface.

Additionally, in a typical implementation, the beneficial effects that the rivets provide in facilitating a reduction in maximum current density and providing a more even distribution of current across the contact surface are particularly prominent when the outermost edge of the electrode is between about 0.5 centimeters and about 1.6 centimeters from a closest edge of the sponge's bottom surface. Therefore, in such instances, a portion of the substantially porous material is exposed at the contact surface between the exposed portion of the first insulating member and edge of the first insulating member that is closest to the exposed portion.

FIGS. 6A-6C show a preassembled electrode interface device 640 that includes upper and lower sponges 610a, 610b held together by rivets 614a/614b and connected to a strap 660. The electrode interface device 640 is supported by the strap by virtue of the strap passing between the upper rivet heads and the upper surface of the upper sponge 610a. The strap can form any part of a device or cap or the like to hold the electrode interface device 640 and other such devices in place against a patient's skin. A space 662 is provided between the upper and lower sponges 610a, 610b to receive an electrode.

A number of embodiments of the invention have been described. Nevertheless, it will be understood that various modifications may be made without departing from the spirit and scope of the invention.

For example, in some implementations, only one of the electrode assemblies (e.g., the anodal electrode) in a system will include a rivet or rivets.

Additionally, in some implementations, the rivet or rivets only pass through the bottom sponge or bottom portion of a sponge in an electrode assembly. In those instances, the rivets play no role in holding components together, but still provide benefits as discussed herein. The rivets and their constituent parts can have a variety of shapes and sizes. Any number and arrangement of rivets can be provided.

The holes that the rivets pass through in the sponge(s) may be pre-formed or may be formed simply by virtue of the shaft portions of the rivets being pushed through the sponge(s).

The electrodes can take a variety of shapes and sizes. They need not be flat, and can be hardwired to the electrical cable that connects to the tDCS device. They also can be permanently connected to the electrode interface assembly. The upper sponge and the lower sponge may actually be simply two parts of the same sponge, separated, for example, by an opening in an edge of the sponge for receiving and gripping the electrode in a manner that facilitates a low resistance electrical connection between the sponge and the electrode.

In some implementations, both electrodes need not be positioned on the patient's head to deliver effective tDCS. Instead, for example, one can be positioned on the patient's head and the other on the patient's neck. Instead of rivets, the insulating members can be a pin pushed into the contact surface of the substantially porous element, a sticker or adhesive material adhered to the contact surface of the substantially porous element.

The insulating portion, such as the rivets, can take on various shapes. The surface of the rivet may slightly protrude from sponge surface. In general, the distance of protrusion should not be so much that a significant portion of the sponge is prevented from touching the body or target surface as a result of the protrusion. For example the protrusion may be up to about 0.5 cm or 0.1 cm. In addition, the surface of the protrusion may be concave or bent. The protruding surface generally has a sufficiently large area such that then the sponge is applied with a typical amount of pressure, for example, as may be provided by a strap, then at least some fluid is ejected from the sponge forming a thin layer between the sponge and the tissue, but the form of the insulator acts to minimize or control the level of fluid between the insulator and the tissue. For example, there may be no significant fluid between the insulator and the tissue.

Application of further pressure to the electrode may cause the sponge to contact the tissue such that there is no significant fluid between the sponge and the tissue. In such case, the insulating portion may press down on the tissue in a manner causing the tissue to deform and a portion of the insulating material to protrude into the tissue. The shape of the protrusion may, in some instances, remove or minimize damage to the tissue. The sponge or strap (e.g., in the form of head-gear) may include a mechanism to control or indicate the level of force or pressure applied to the electrode. For example a tightening mechanism on a strap may be adjusted to provide a preferred amount of force or pressure on the electrode. The tightening mechanism or a separate mechanism may provide a direct or indirect indication of the pressure or force. The tightening mechanism may control the level of pressure or force applied for example by releasing tightness when a level is exceeded.

Accordingly, other implementations are within the scope of the claims.

What is claimed is:
1. An electrode assembly comprising:
a substantially porous electrode sponge configured to be coupled to an electrode for delivery of electrical current to a patient in a neurostimulation procedure, the substantially porous electrode sponge material defining an outer surface comprising a first portion and a second portion, wherein the first portion of the outer surface contacts the patient during the neurostimulation procedure;

an electrolytic solution contained within the electrode sponge for facilitating electrical conduction between the outer surface of the sponge and the patient; and a first insulating member coupled to the substantially porous electrode sponge, the first insulating member being electrically non-conductive and having an outer surface exposed at the outer surface of the substantially porous electrode sponge, the outer surface of the first insulating member together with the first portion of the outer surface of the substantially porous electrode sponge forming a patient contact surface for contacting the patient during the neurostimulation procedure, wherein the outer surface of the first insulating member prevents the second portion of the outer surface of the substantially porous electrode sponge from contacting the patient to deliver the electrical current during the neurostimulation procedure.

2. The electrode assembly of claim 1 wherein the substantially porous electrode sponge has one or more edges that extend from the outer surface, and wherein the first insulating member is exposed at the outer surface near one of the edges.

3. The electrode assembly of claim 2 wherein the first insulating member is positioned so that an outermost point of the exposed portion is no further from the nearest edge than approximately 50% of the exposed portion's width.

4. The electrode assembly of claim 1 wherein the substantially porous electrode sponge has a corner at a point where the outer surface and two of the edges connect to one another and the first insulating member is exposed at the outer surface near the corner.

5. The electrode assembly of claim 1 wherein the substantially porous electrode sponge has one or more edges at which an opening is provided for receiving and gripping the electrode in a manner that facilitates a low resistance electrical connection between the substantially porous electrode sponge and the electrode.

6. The electrode assembly of claim 1 wherein a portion of the substantially porous electrode sponge material is exposed at the contact surface between the exposed portion of the first insulating member and edge of the first insulating member that is closest to the exposed portion.

7. The electrode assembly of claim 1 wherein the substantially porous electrode sponge comprises:

a first planar layer; and a second planar layer disposed substantially parallel with the first planar layer, wherein the first insulating member is configured to physically hold together the first layer and the second layer.

8. The electrode assembly of claim 7 wherein the first insulating member comprises:

a substantially cylindrical portion that extends through the first and second layers of the substantially porous electrode sponge; and a head at each end of the substantially cylindrical portion, wherein each head has a larger diameter than the substantially cylindrical portion.

9. The electrode assembly of claim 7 wherein the first insulating member is a rivet.

10. The electrode assembly of claim 1 wherein the first insulating member is selected from the group consisting of a pin pushed into the outer surface of the substantially porous electrode sponge and a sticker or adhesive material adhered to the outer surface of the substantially porous element.

11. The electrode assembly of claim 1 wherein the substantially porous electrode sponge is configured to absorb and at least partially contain the electrolytic solution in liquid form.

12. The electrode assembly of claim 1 further comprising: a second insulating member coupled to the substantially porous electrode sponge and exposed at the outer surface, wherein the first and second insulating members are spaced sufficiently far apart from one another so that the electrode can fit between the first and second insulating members.

13. An electrode assembly comprising:

a substantially porous element having an outer surface, at least a first portion of which is configured to contact a patient during delivery of electrical current from the substantially porous element to the patient during a neurostimulation procedure, wherein the substantially porous element includes a first layer and a second layer;

an electrode sandwiched between the first and second layers of the porous element; and two or more rivets made of electrically insulating material passing through the first layer and the second layer of the substantially porous element to hold the first and second layers portion together, wherein each rivet is electrically non-conductive and has a head portion with an outer surface exposed at the outer surface of the substantially porous element, the outer surfaces of the rivets together with the first portion of the outer surface of the substantially porous element forming a patient contact surface for contacting the patient during the neurostimulation procedure, and wherein the outer surfaces of the rivets prevent at least a second portion of the outer surface of the substantially porous element from contacting the patient during the neurostimulation procedure, and wherein the rivets are positioned so that an innermost portion of each respective head is no further from a closest edge of the substantially porous element than approximately 150% of the head's diameter.

14. A system comprising:

a neurostimulation device;

at least two electrically conductive cables coupled to the neurostimulation device;

an electrode coupled to the distal end of each respective one of the electrically conductive cables; and an electrode interface coupled to at least one of the electrodes, each electrode interface comprising:

a substantially porous electrode sponge physically coupled to the electrode for delivery of electrical current to a patient in a neurostimulation procedure, the substantially porous material defining an outer surface, wherein at least a first portion of the outer contact surface contacts the patient during the neurostimulation procedure; and a first insulating member coupled to the substantially porous electrode sponge, the first insulating member being electrically non-conductive and having an outer surface exposed at the outer surface of the substantially porous electrode sponge, the outer surface of the first insulating member together with the first portion of the outer surface of the substantially porous electrode sponge forming a patient contact surface for contacting the patient during the neurostimulation procedure, wherein the outer surface of the first insulating member prevents at least a second portion of the outer surface from contacting the patient to deliver the electrical current during the neurostimulation procedure.

15. The system of claim 14 wherein the substantially porous electrode sponge has one or more edges that extend from the outer surface, and wherein the first insulating member is positioned so that an outermost point of the exposed portion is no further from the nearest edge than approximately 50% of the exposed portion's width.

16. The system of claim 14 wherein the substantially porous electrode sponge has a corner at a point where the outer surface and two of the edges connect to one another and the first insulating member is exposed at the contact surface near the corner.

17. The system of claim 14 wherein the substantially porous electrode sponge has one or more edges at which an opening is provided for receiving and gripping the electrode in a manner that facilitates a low resistance electrical connection between the substantially porous electrode sponge and the electrode.

18. The system of claim 14 wherein a portion of the substantially porous electrode sponge is exposed at the contact surface between the exposed portion of the first insulating member and edge of the first insulating member that is closest to the exposed portion.

19. The system of claim 14 wherein the substantially porous electrode sponge comprises a first layer and a second layer, wherein the first insulating member is configured to physically hold together the first layer and the second layer and the electrode is positioned between the first layer and the second layer of the substantially porous electrode sponge.

20. The system of claim 19 wherein the first insulating member is a rivet with a substantially cylindrical portion that extends through the first and second layers of the substantially porous electrode sponge and a head at each end of the substantially cylindrical portion, wherein each head has a larger diameter than the substantially cylindrical portion.

21. The system of claim 14 further comprising: a second insulating member coupled to the substantially porous electrode sponge and exposed at the outer surface of the substantially porous electrode sponge, wherein the first and second insulating members are spaced sufficiently far apart from one another so as to accommodate the electrode, which is positioned between the first and second insulating members.

22. The system of claim 14 further comprising: a second insulating member coupled to the substantially porous electrode sponge and exposed at the outer surface, wherein the first and second insulating members are exposed at a surface of the substantially porous electrode sponge opposite the outer surface, the system further comprising: a strap for coupling the electrode interface to the patient, wherein the strap is between portions of the first and second insulating members that are exposed at the surface of the substantially porous material opposite the outer surface and the portions of the first and second insulating members extend over the strap to thereby couple the electrode interface to the strap.

23. The system of claim 14 wherein the first insulating member is selected from the group consisting of a pin pushed into the outer surface of the substantially porous element and a sticker or adhesive material adhered to the outer surface of the substantially porous electrode sponge.

24. The system of claim 14 wherein the substantially porous electrode sponge contains an electrolyte in liquid form.

* * * * *